United States Patent
Fujii

(10) Patent No.: US 10,709,430 B2
(45) Date of Patent: Jul. 14, 2020

(54) VEIN DISSECTING DEVICE AND METHOD

(71) Applicant: TERUMO KABUSHIKI KAISHA, Shibuya-ku, Tokyo (JP)

(72) Inventor: Tatsunori Fujii, Ebina (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 653 days.

(21) Appl. No.: 15/293,004

(22) Filed: Oct. 13, 2016

(65) Prior Publication Data

US 2017/0100108 A1 Apr. 13, 2017

Related U.S. Application Data

(60) Provisional application No. 62/240,663, filed on Oct. 13, 2015, provisional application No. 62/240,668, (Continued)

(51) Int. Cl.
*A61B 17/00* (2006.01)
*A61B 17/32* (2006.01)
(Continued)

(52) U.S. Cl.
CPC .... *A61B 17/00008* (2013.01); *A61B 1/00195* (2013.01); *A61B 1/018* (2013.01); *A61B 1/051* (2013.01); *A61B 1/0676* (2013.01); *A61B 17/320016* (2013.01); *A61B 17/32053* (2013.01); *A61B 18/08* (2013.01); *A61B 18/082* (2013.01); *A61B 18/10* (2013.01); *A61B 18/148* (2013.01); *A61B 90/361* (2016.02); *A61B 2017/00261* (2013.01); *A61B 2017/00969* (2013.01); *A61B 2017/320044* (2013.01); *A61B 2017/320064* (2013.01); *A61B 2018/00404* (2013.01); *A61B 2018/00428* (2013.01); *A61B 2018/00577* (2013.01); *A61B 2018/00589* (2013.01); *A61B 2018/00601* (2013.01);
(Continued)

(58) Field of Classification Search
CPC ...... A61B 17/32053; A61B 17/320016; A61B 17/00008; A61M 1/0078
See application file for complete search history.

(56) References Cited

U.S. PATENT DOCUMENTS

| 6,036,713 A * | 3/2000 | Kieturakis | A61B 17/00008 606/159 |
| 2006/0211916 A1* | 9/2006 | Kasahara | A61B 17/00008 600/114 |
| 2008/0255600 A1* | 10/2008 | Braam | A61B 17/00008 606/190 |

* cited by examiner

*Primary Examiner* — Diane D Yabut
(74) *Attorney, Agent, or Firm* — Buchanan Ingersoll & Rooney PC

(57) ABSTRACT

A vein harvesting device for harvesting a vein in a living body includes an elongated hollow member possessing a distal end portion and a proximal end portion, and a dissecting member at the distal end portion of the elongated hollow member and configured to dissect tissue in the body surrounding the vein during harvesting of the vein, wherein the dissecting member possessing a proximal end portion communicating with the elongated hollow member. The dissecting member possesses two side portions, with each of the side portions possessing a first end at an end of the side portion farther from the hollow member and a second end at an end of the side portion closer to the hollow member. A projection projects from the first end at each of the side portions of the dissecting member to contact the tissue in the body surrounding the vein during the harvesting of the vein.

13 Claims, 31 Drawing Sheets

Related U.S. Application Data filed on Oct. 13, 2015, provisional application No. 62/240,797, filed on Oct. 13, 2015, provisional application No. 62/240,834, filed on Oct. 13, 2015.

(51) Int. Cl.
| | | |
|---|---|---|
| *A61B 17/3205* | (2006.01) | |
| *A61B 1/00* | (2006.01) | |
| *A61B 1/018* | (2006.01) | |
| *A61B 1/05* | (2006.01) | |
| *A61B 1/06* | (2006.01) | |
| *A61B 18/08* | (2006.01) | |
| *A61B 18/10* | (2006.01) | |
| A61B 18/14 | (2006.01) | |
| A61B 90/00 | (2016.01) | |
| A61B 18/00 | (2006.01) | |

(52) U.S. Cl.
CPC .............. *A61B 2018/00982* (2013.01); *A61B 2090/08021* (2016.02)

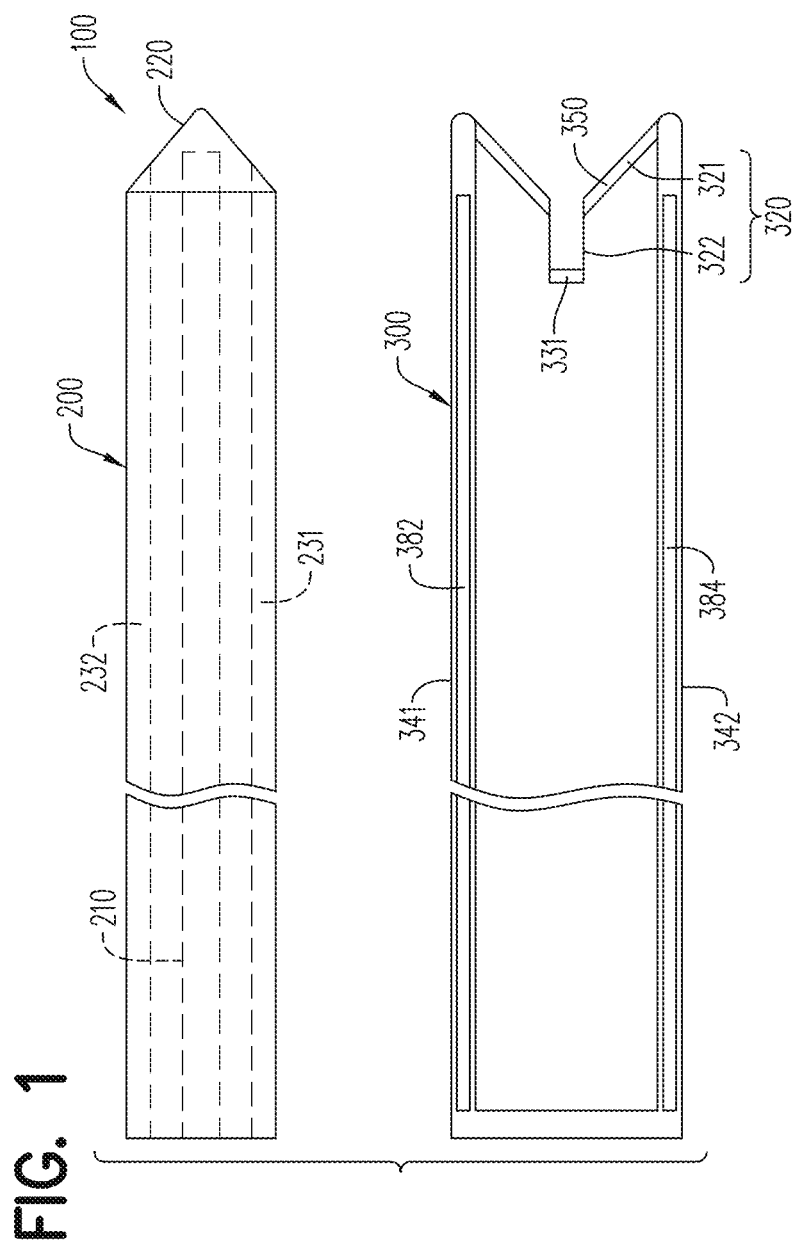

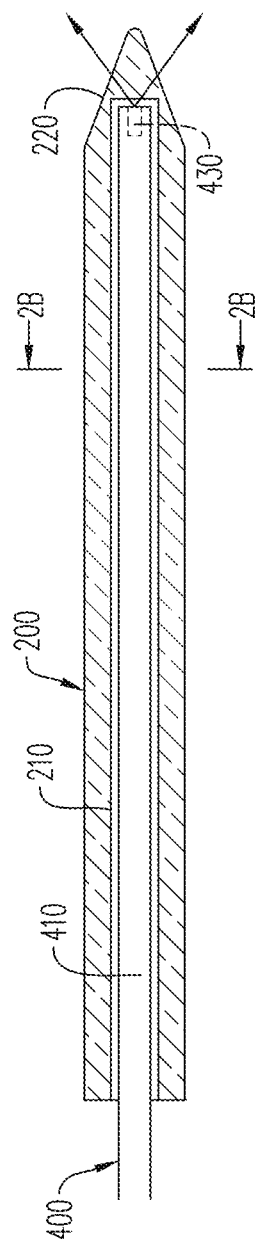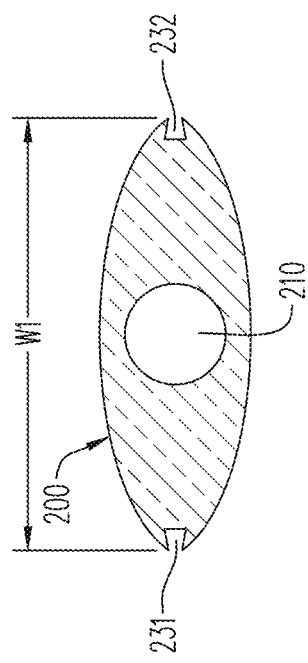
FIG. 2A
FIG. 2B

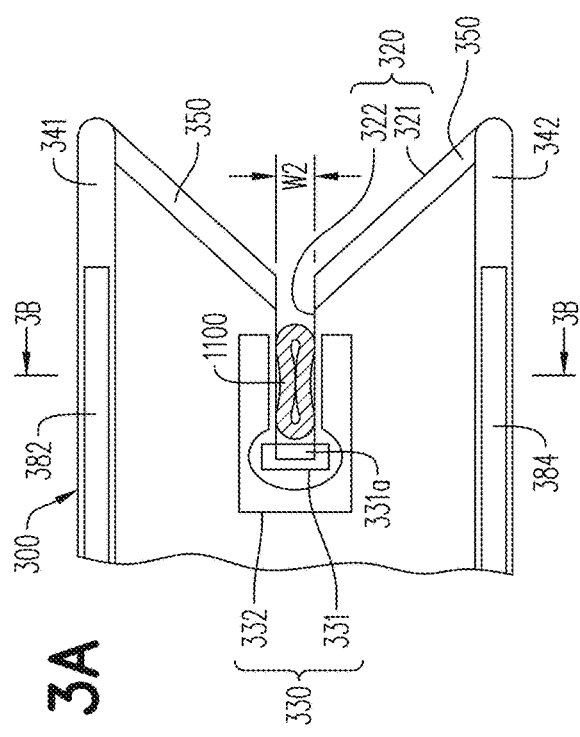
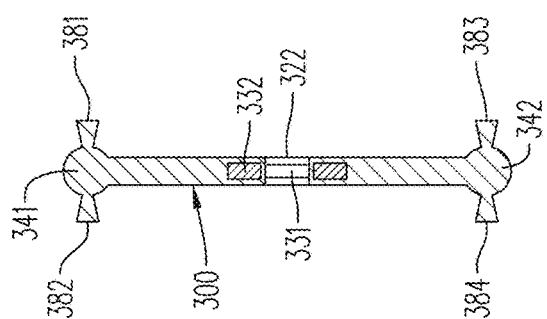
FIG. 3A
FIG. 3B

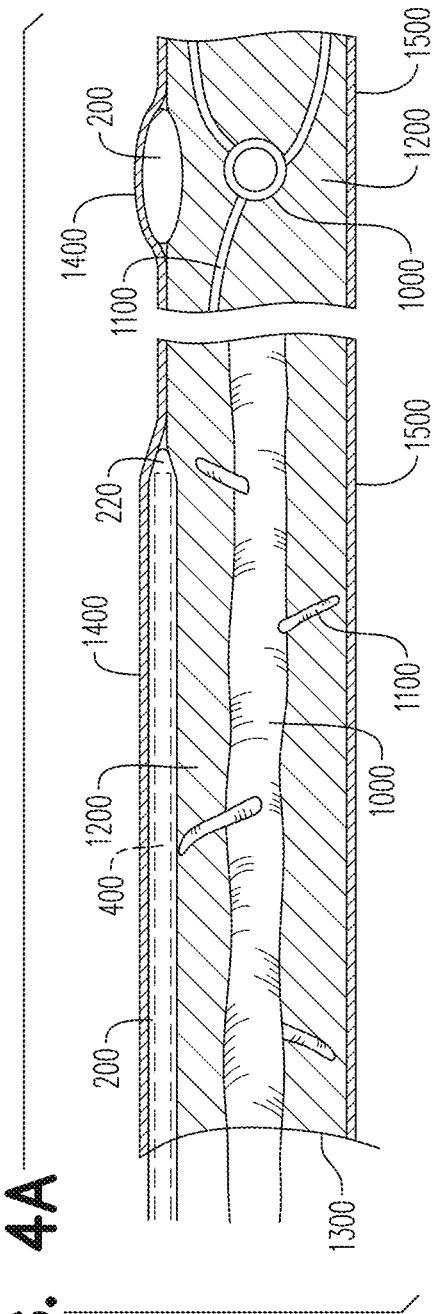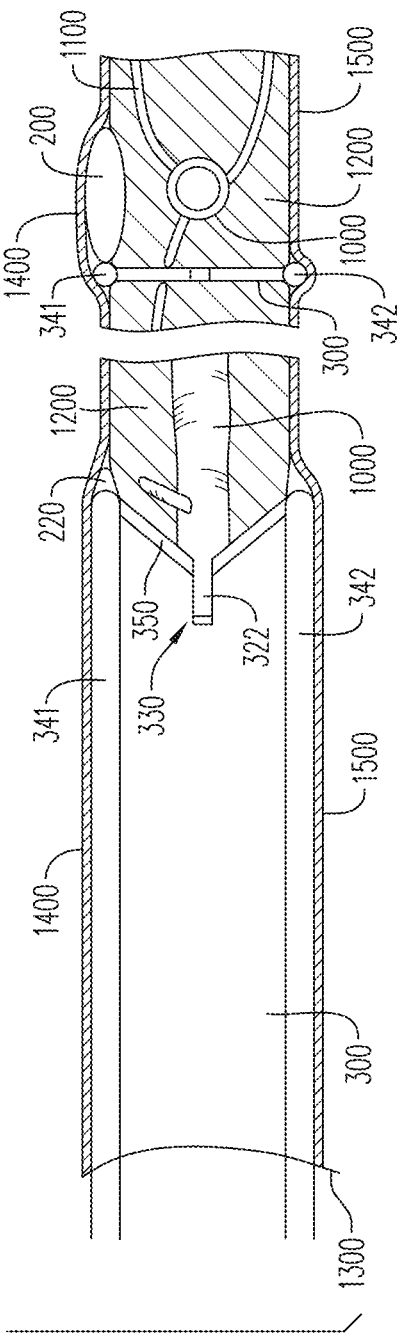

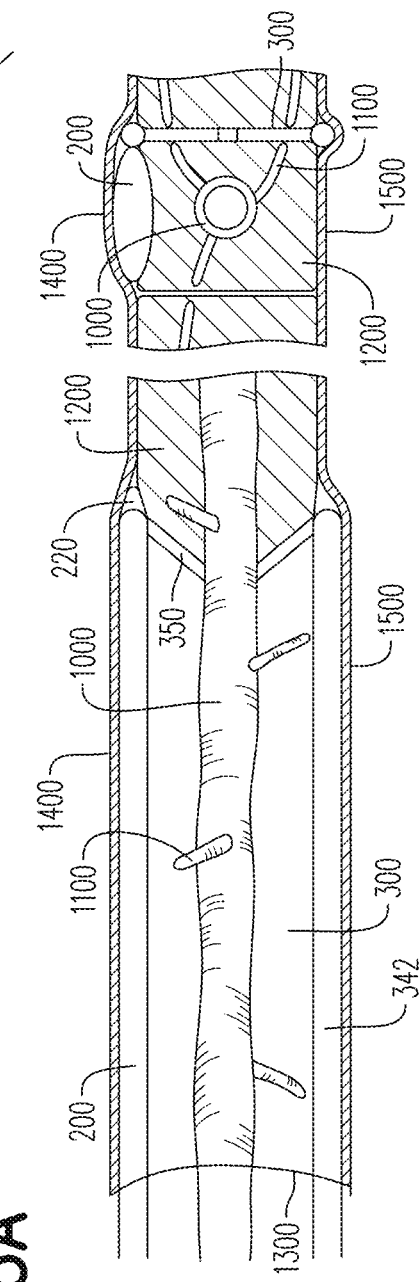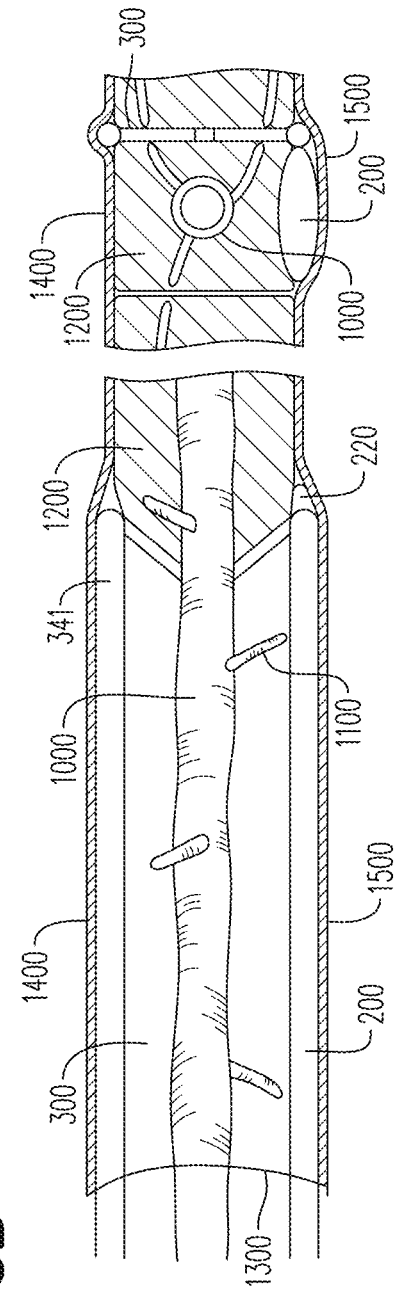

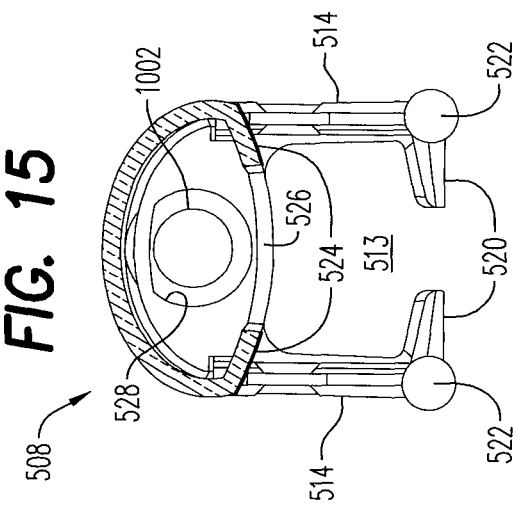
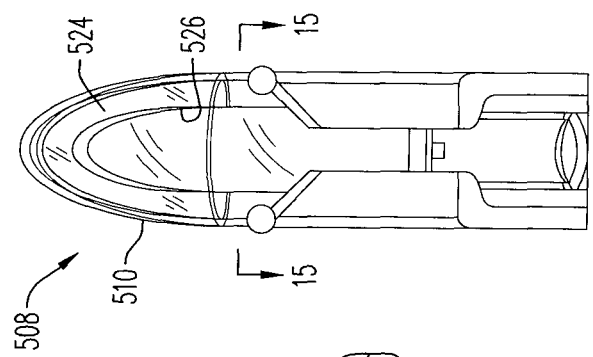
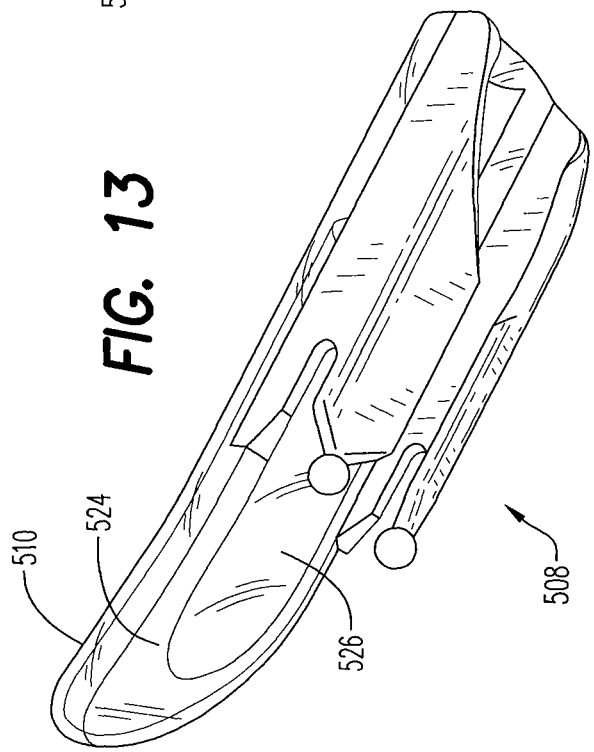

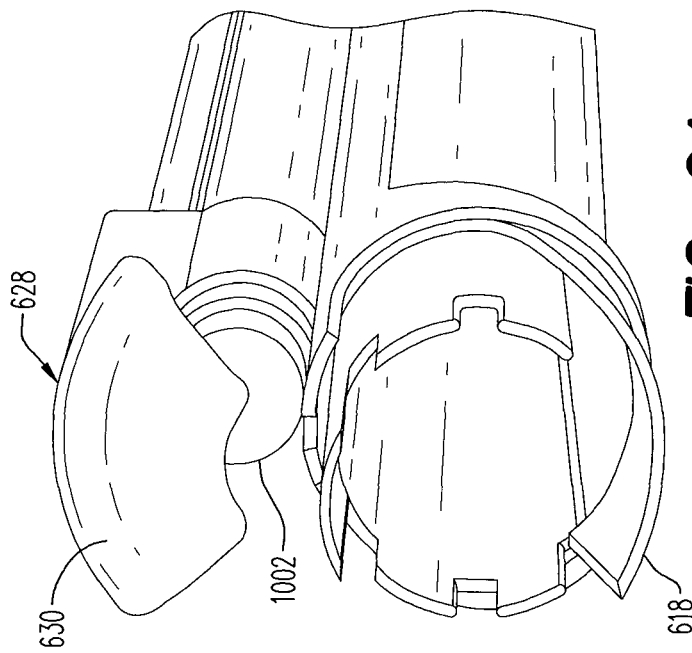
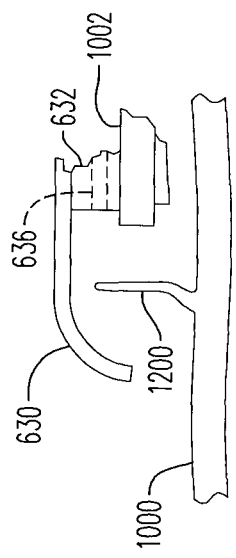
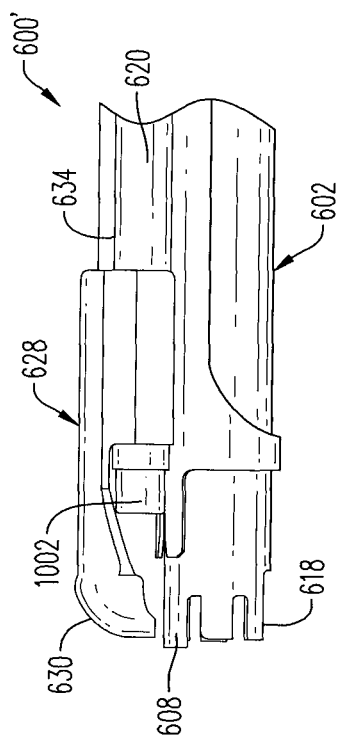
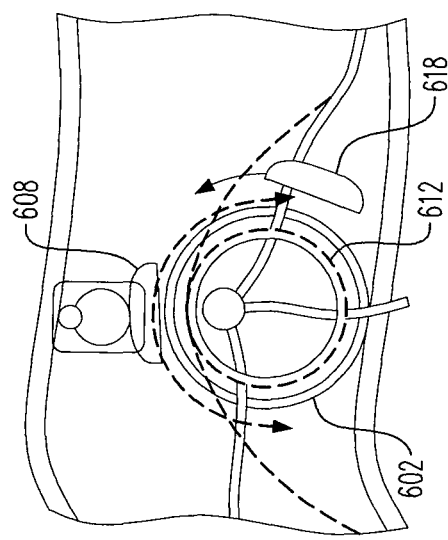
FIG. 23
FIG. 24
FIG. 25
FIG. 26

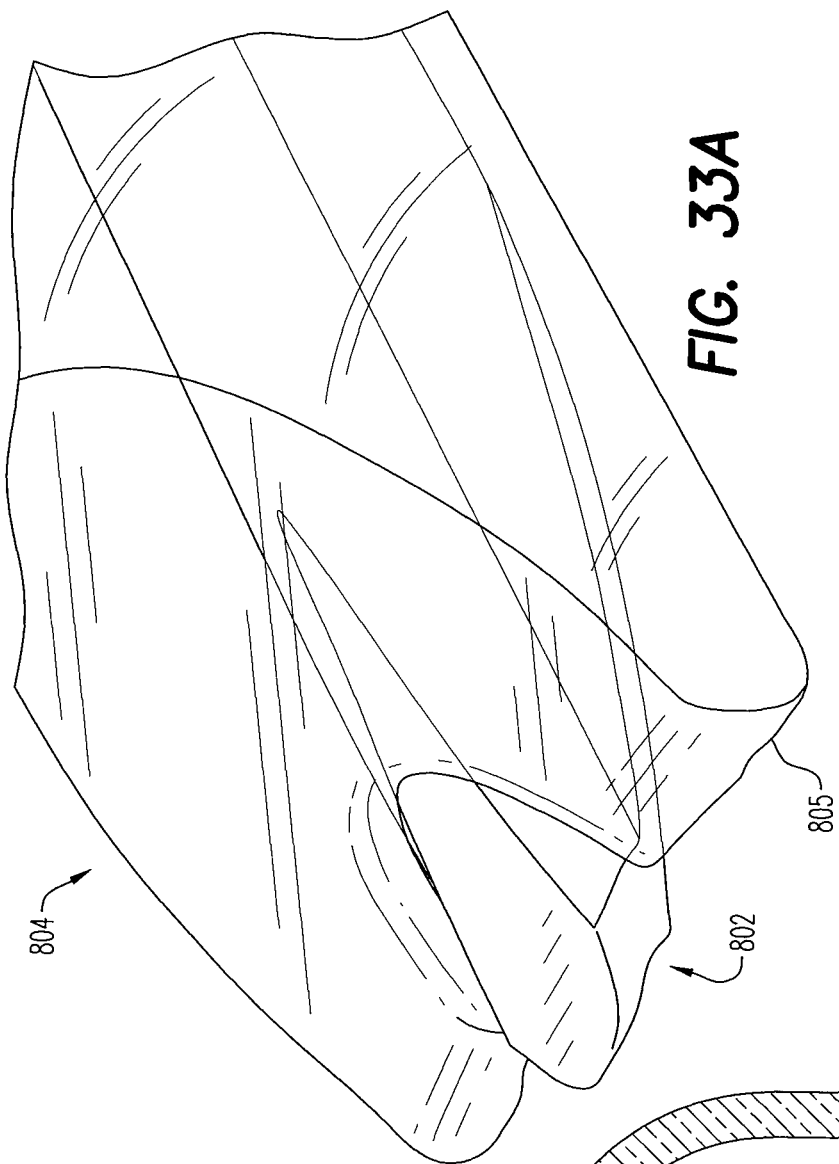
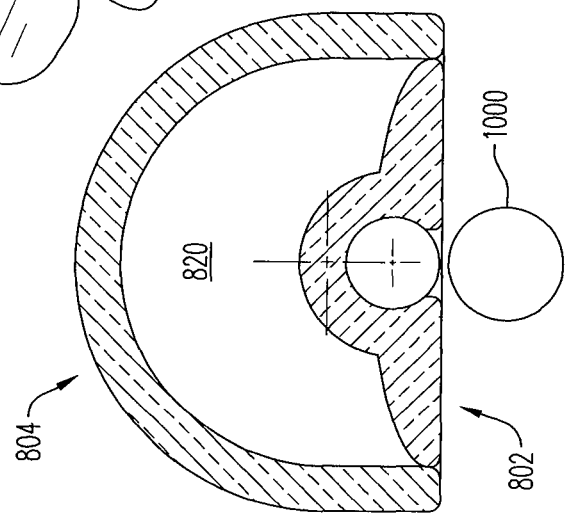

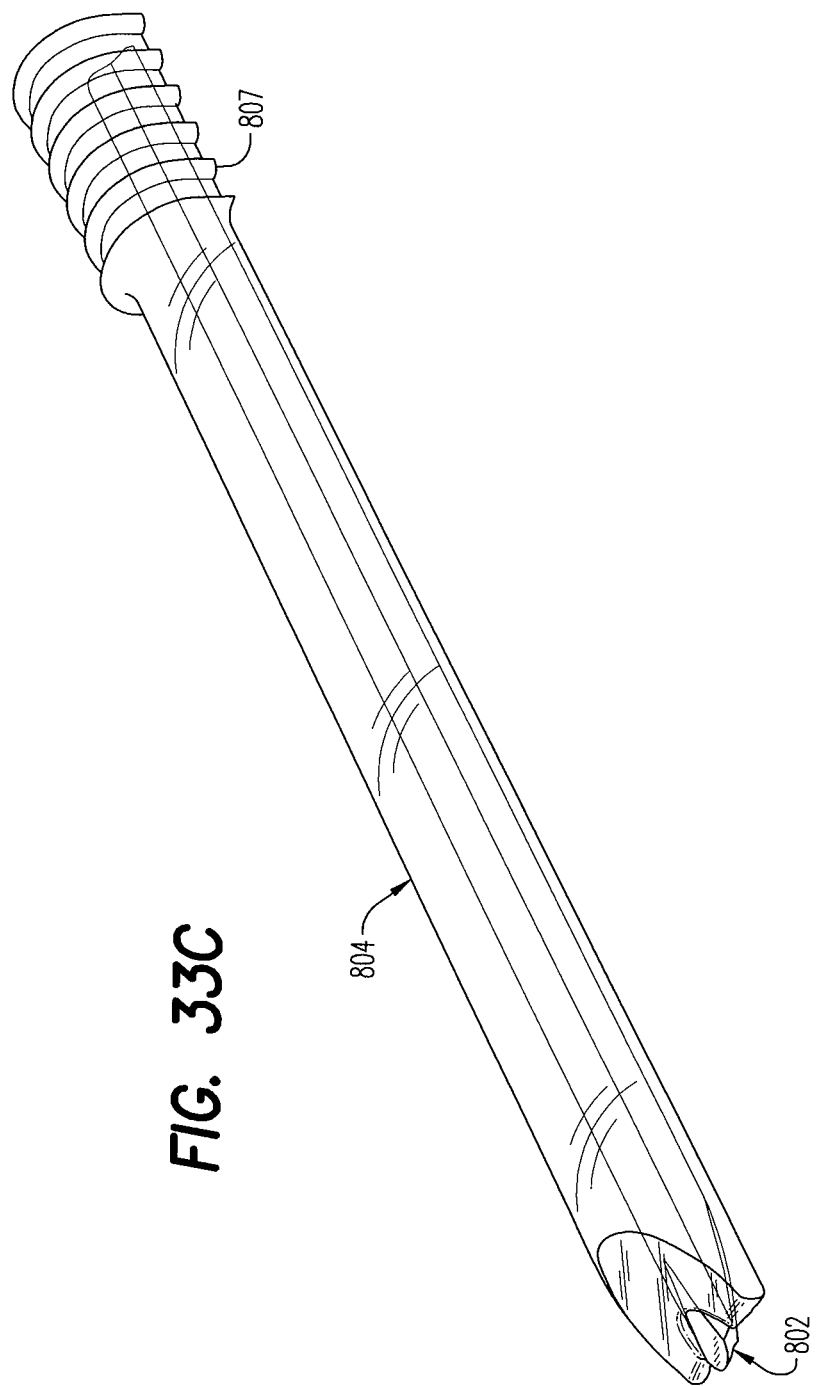

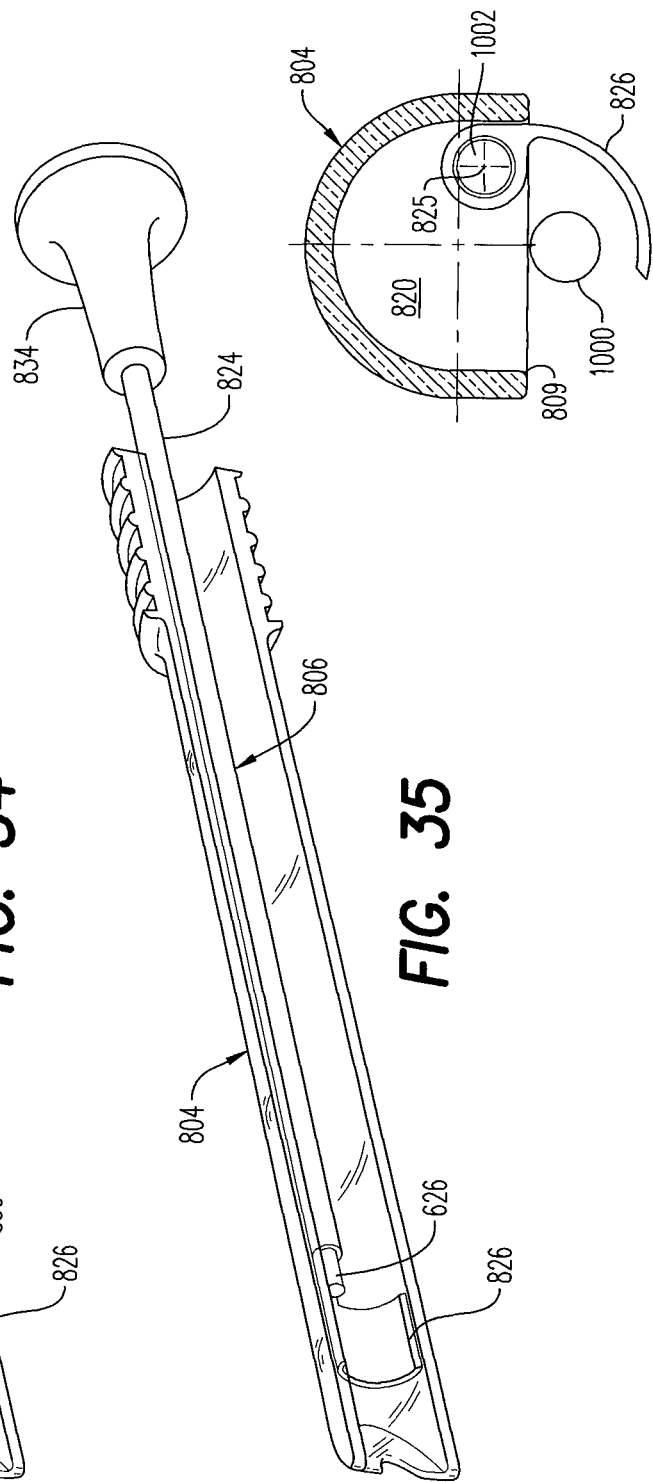

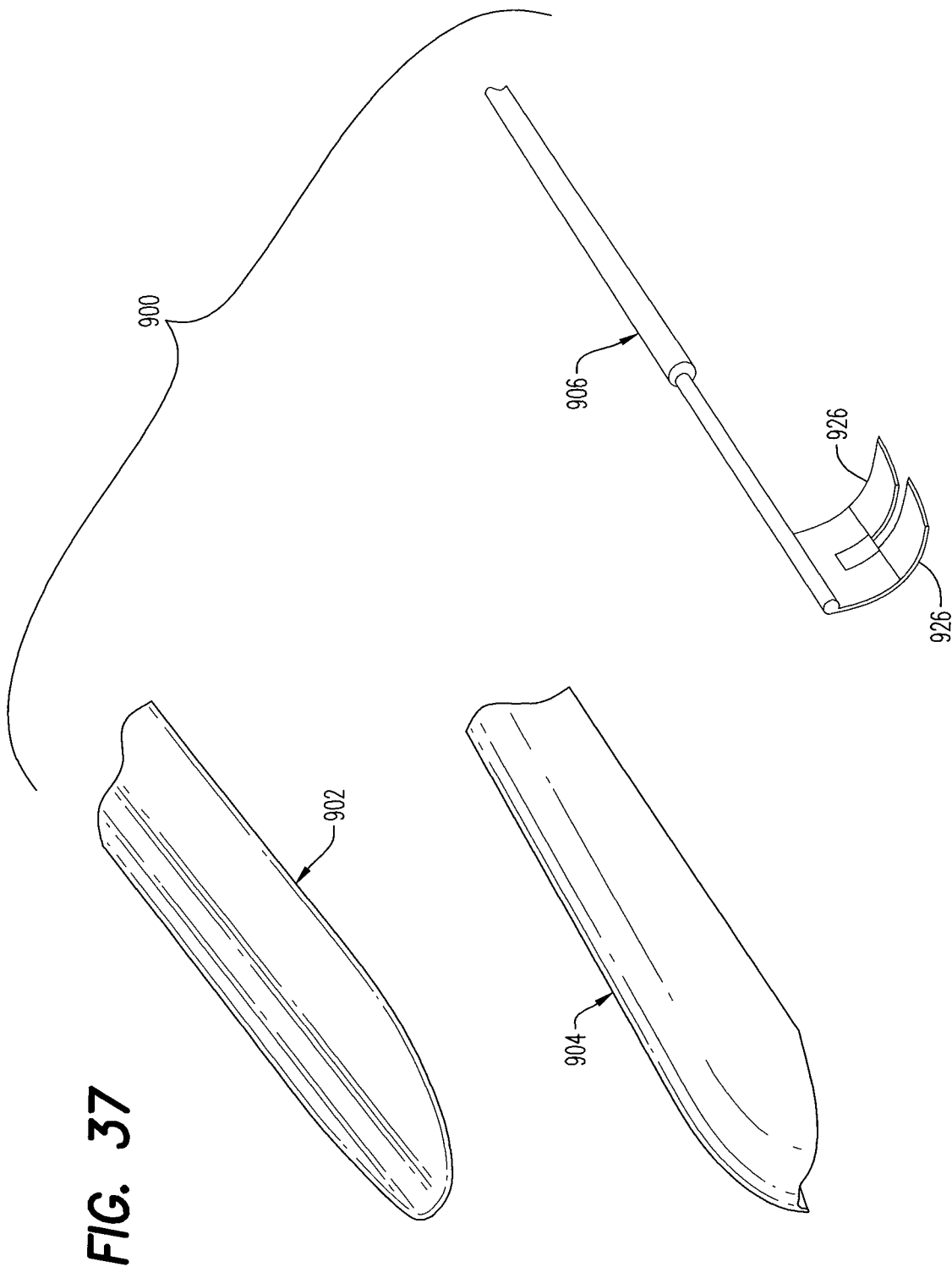

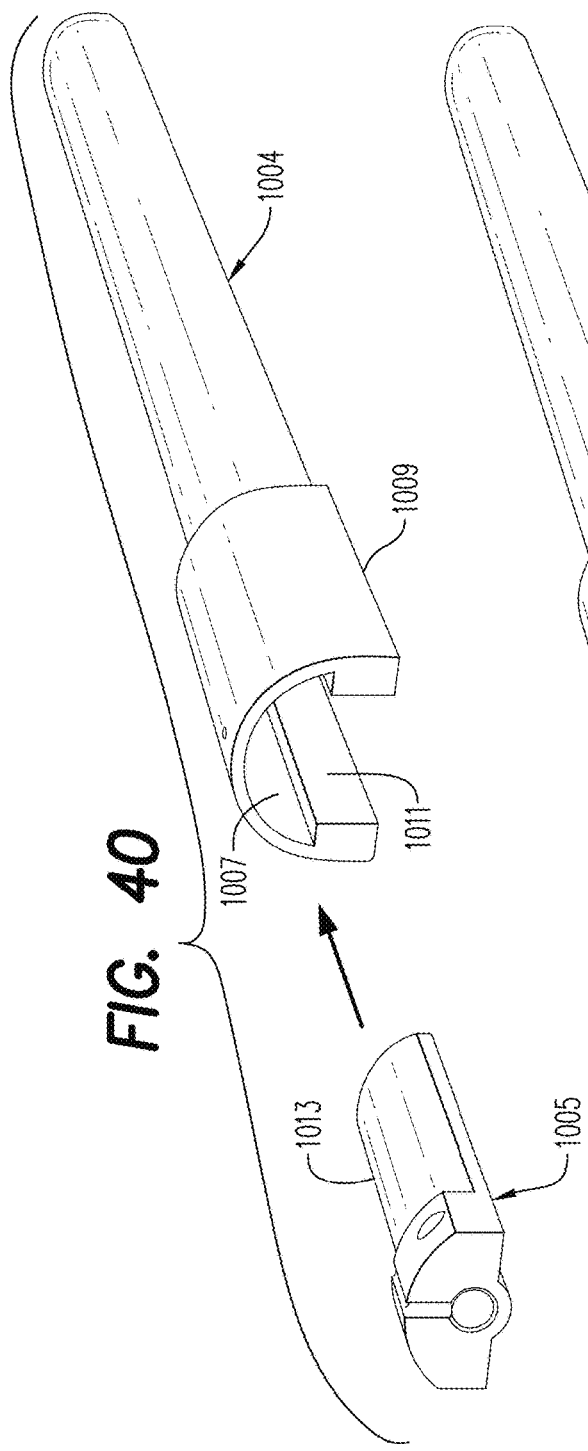

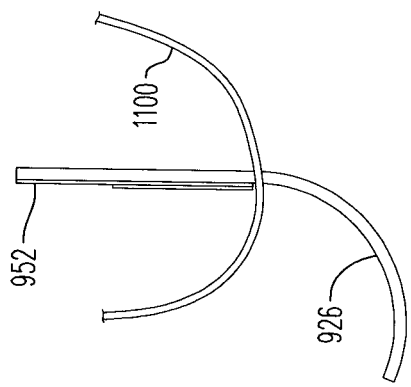
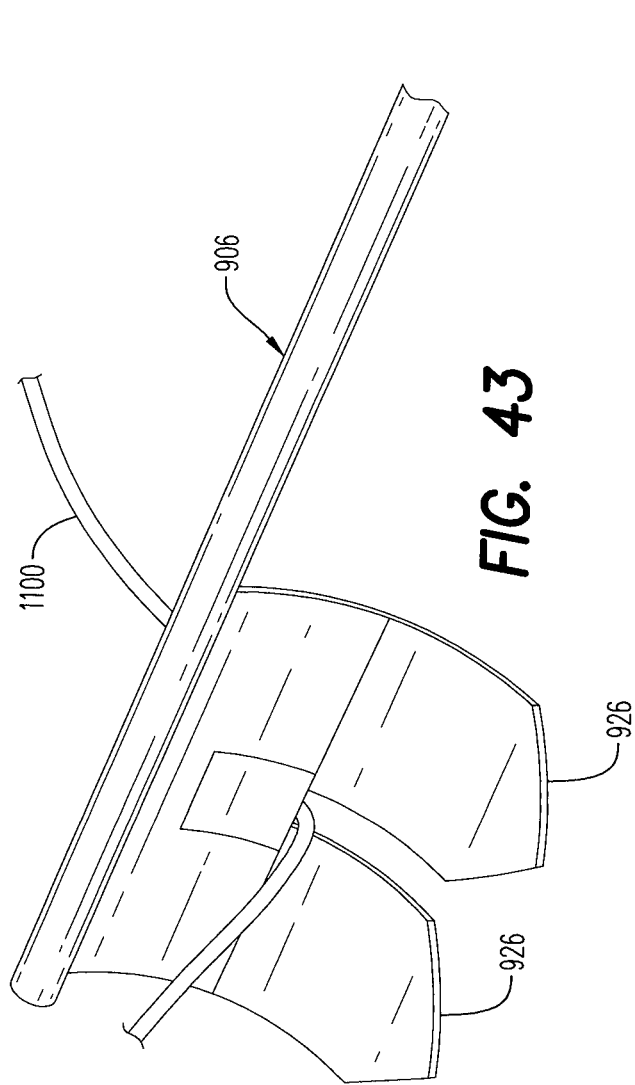
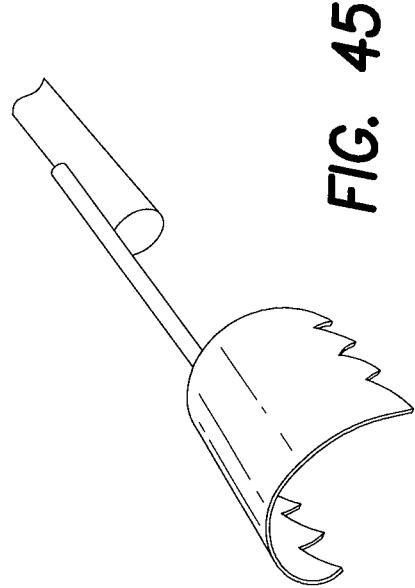

VEIN DISSECTING DEVICE AND METHOD

This application claims priority under 35 U.S.C. § 119(e) to U.S. Provisional Application No. 62/240,663, U.S. Provisional Application No. 62/240,668, U.S. Provisional Application No. 62/240,797, and U.S. Provisional Application No. 62/240,834 filed on Oct. 13, 2015, the entire content of each of which is incorporated herein by reference.

TECHNICAL FIELD

The present disclosure relates to a device for dissecting or harvesting a vein in a living body.

BACKGROUND DISCUSSION

It is known to use an artery graft (e.g., internal thoracic artery, gastroepiploic artery and radial artery) or a vein graft (e.g., great saphenous vein) as a bypass vessel in performing vascular bypass grafting at the heart (coronary artery bypass grafting: CABG). It has been reported that. at present, artery grafts (particularly, internal thoracic artery) offer higher long-term patency rates than vein grafts. Vein grafts are commonly thought to be poor in long-term patency rate. In recent years, however, it has been reported that the long-term patency rate of vein grafts is enhanced when the vein graft is harvested in a state in which the vein is covered by surrounding tissue (for example, fat, connective tissue, tissue between a skin layer and a muscle layer, tissue between a skin layer and an interosseous membrane, branch vessels, etc.) and is used as a bypass vessel while remaining covered with the tissue.

Generally speaking, there are two primary techniques for harvesting blood vessels such as the saphenous vein. One technique is referred to as open vein harvesting. This technique involves making an elongated incision along, for example, the patient's limb (leg), and then carrying out the harvesting procedure for removing the blood vessel from the patient's limb. This technique has been found to be somewhat problematic in that it is rather invasive, requiring a rather extensive incision in the patient's limb. Harvesting site complications (e.g., infections) are also not uncommon.

Another technique is referred to as endoscopic vein harvesting. This technique has some advantages over open vein harvesting in that the endoscopic vein harvesting is less invasive and has been found to have a lower incidence of infection. Unfortunately, endoscopic vein harvesting exhibits a lower patency rate because the harvested vein tends to be more damaged.

SUMMARY

The devices and methods disclosed here provide a technique having an improved patency rate similar to the patency rate with the open vein harvesting, but without the harvesting site complications. The technique disclosed here is referred to as a no-touch technique. This technique improves endothelial integrity while reducing injury to the blood vessel (vein). It has also been found that this technique delays arterial atherosclerotic processes, conserves the vasa vasorum and it promotes the nitric oxide synthase activity of endothelial cells.

According to one aspect, a vein harvesting device for harvesting a vein in a living body includes an elongated hollow member possessing a distal end portion and a proximal end portion, and a dissecting member at the distal end portion of the elongated hollow member and configured to dissect tissue in the body surrounding the vein during harvesting of the vein, wherein the dissecting member possessing a proximal end portion communicating with the elongated hollow member. The dissecting member possesses two side portions, with each of the side portions possessing a first end at an end of the side portion farther from the hollow member and a second end at an end of the side portion closer to the hollow member. A projection projects from the first end at each of the side portions of the dissecting member to contact the tissue in the body surrounding the vein during the harvesting of the vein.

In accordance with another aspect, a vein harvesting device for harvesting a vein in a body comprises: an elongated hollow member possessing a distal end portion and a proximal end portion; and a dissecting member at the distal end portion of the elongated hollow member, with the dissecting member possessing a pair of spaced apart side portions projecting away from the distal end portion of the elongated hollow member, and with each side portion possessing a first end at an end of the side portion farther from the hollow member portion and a second end at an end of the side portion closer to the hollow member. The distal end portion of each side portion possesses a groove that is open at its distal end, extends toward the proximal end portion of the side member, and terminates at a cutting member configured to cut a side branch of the vein during harvesting of the vein, and a projection projects from each of the side portions of the dissecting member to contact a tissue in the body surrounding the vein during the harvesting of the vein.

According to another aspect, a vein harvesting method for harvesting a vein in a body comprises: contacting the distal end portion of a dissecting member and a projection of the dissecting member on a body while inclining the dissecting member to the body, and inserting a distal end portion of the dissecting member that is positioned at a distal end of an elongated hollow member into the body after puncturing the body with the projection of the dissecting member and inserting the projection of the dissecting member into the body. The dissecting member is inserted into the body by operating the elongated hollow member, and the dissecting member possesses a distal end portion and two spaced apart side portions projecting in a direction away from the distal end portion. The method further includes positioning the dissecting member relative to the vein such that the vein is between the two side portions of the dissecting member; forward moving the dissecting member along the vein while the distal end portion of the dissecting member separates the vein from tissue around the vein; removing the dissecting member from the body; cutting and closing distal and proximal ends of the separated vein; and removing the separated vein from the body.

BRIEF DESCRIPTION OF THE DRAWINGS

FIG. 1 is a plan view of a blood vessel dissecting device according to a first embodiment of the present disclosure.

FIGS. 2A and 2B illustrate a dissecting device forming a part of the blood vessel dissecting device shown in FIG. 1, wherein FIG. 2A is a longitudinal cross-sectional view and FIG. 2B is a transverse cross-sectional view taken along the section line 2B-2B of FIG. 2A.

FIGS. 3A and 3B illustrate a cutting device forming a part of the blood vessel dissecting device shown in FIG. 1, wherein FIG. 3A is a plan view and FIG. 3B is a cross-sectional view taken along the section line 3B-3B of FIG. 3A.

FIGS. 4A and 4B show views explaining a blood vessel dissecting method carried out using the blood vessel dissecting device shown in FIG. 1.

FIGS. 5A and 5B show views explaining the blood vessel dissecting method carried out using the blood vessel dissecting device shown in FIG. 1.

FIGS. 13-15 depict a bottom perspective view, a bottom view and a front view respectively of the dissecting member illustrating the frame bordering the window of the upturned distal end portion of the dissecting member.

FIG. 23 is a side view of a part of the dissecting device shown in FIG. 22.

FIG. 24 is a front perspective view of a part of the dissecting device shown in FIG. 22.

FIG. 25 is a front view of the dissecting member forming a part of the dissecting device shown in FIG. 22 illustrating the way in which the dissecting member interacts with the vein being dissected.

FIG. 26 is a side view of a part of the dissecting device shown in FIG. 22 illustrating the way in which the dissecting member interacts with a side branch of a vein being dissected.

FIG. 33A is a perspective view of a part of the dissecting member and covering member forming a part of the dissecting device illustrated in FIG. 30.

FIG. 33B is a cross-sectional view of the dissecting member and covering member forming a part of the dissecting device illustrated in FIG. 30.

FIG. 33C is a perspective view of the dissecting member and covering member forming a part of the dissecting device illustrated in FIG. 30.

FIG. 34 is a perspective view of the covering member and the cutting member forming a part of the dissecting device illustrated in FIG. 30.

FIG. 35 is a perspective view of the covering member and the cutting member, with a viewing forming a part of the dissecting device illustrated in FIG. 30.

FIG. 36 is a cross-sectional view of the covering member and the cutting member forming a part of the dissecting device illustrated in FIG. 30.

FIG. 37 is a top perspective view of another embodiment of the dissecting device.

FIGS. 40-42 are top perspective views of another embodiment of the covering member used in the disclosed dissecting devices.

FIG. 43 is a perspective view of another embodiment of the cutting member used in the disclosed dissecting devices.

FIG. 44 is a schematic side view of the cutting member shown in FIG. 43.

FIG. 45 is an illustration of another embodiment of the cutting member used in the disclosed dissecting devices.

DETAILED DESCRIPTION

Figure 6:
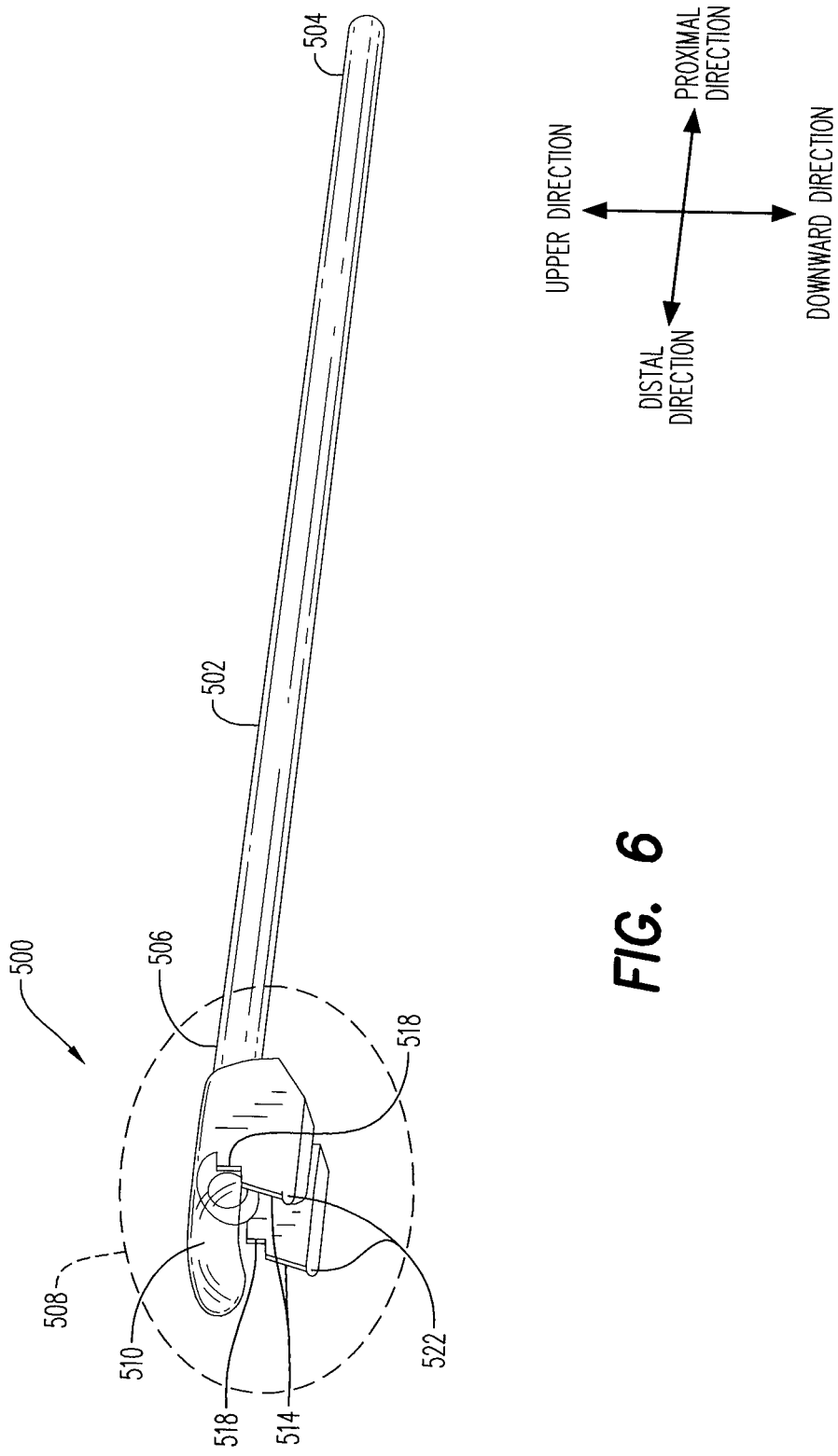
FIG. 6 is a perspective view of a dissecting device according to another embodiment.

Examples of a blood vessel dissecting device and a blood vessel dissecting method disclosed here will be described in detail below, referring to the attached drawings.

FIGS. 1-5B illustrate a blood vessel dissecting device and blood vessel dissecting method carried out using the blood vessel dissecting device according to a first embodiment representing one example of the vein dissecting device and method disclosed here. In the following description, for convenience of explanation, the right side in FIG. 1 is referred to as the "distal" side or end, and the left side in the figure is referred to as the "proximal" side or end.

A blood vessel (vein) dissecting device 100 shown in FIG. 1 is a device used to dissect or harvest a blood vessel for use as a bypass vessel in carrying out blood vessel bypass grafting (particularly, coronary artery bypass grafting: CABG). Using this blood vessel dissecting device 100, a blood vessel can be harvested in the state of being covered with the surrounding tissue (fat, connective tissue, etc.), preferably to the extent that the blood vessel is not exposed to the surface of the surrounding tissue and the blood vessel does not have the lateral surface that is exposed to the external atmosphere. More preferably, to the extent that an outer surface of the blood vessel is not exposed to the surface of the surrounding tissue and the outer surface of the blood vessel does not have the lateral surface that is exposed to the external atmosphere. The blood vessel to be harvested using the blood vessel dissecting device 100 is not particularly limited insofar as it is a blood vessel that can be used as a bypass vessel. Examples of the applicable blood vessel include internal thoracic artery, gastroepiploic artery, radial artery, and great saphenous vein.

It is preferable, however, that the blood vessel to be harvested is the great saphenous vein. The blood vessel dissecting device 100 and method disclosed here facilitate harvesting or dissecting a blood vessel in the state in which the blood vessel is covered with the surrounding tissue. Harvesting the great saphenous vein using the blood vessel dissecting device 100 and method disclosed here, and using the harvested or dissected vein as a bypass vessel enhances long-term patency rate after the bypass grafting operation. In view of this, in the following, examples of harvesting or dissecting a great saphenous vein by use of the blood vessel dissecting device 100 and method disclosed here will be described as representative of a blood vessel to which the device and method disclosed here are applicable.

As shown in FIG. 1, the blood vessel dissecting device 100 includes or possesses a dissecting device 200 and a cutting device 300. Both the dissecting device 200 and the cutting device 300 are devices which are inserted into a living body along the great saphenous vein. The dissecting device 200 and the cutting device 300 will now be described in detail below. The dissecting device 200 and the cutting device 300 may be used in other than a living body. For example, the dissecting device 200 and the cutting device 300 can be used with other bodies such as a cadaver and a simulator intended to simulate the living body.

The dissecting device 200 has an elongated bar-like shape (bar-shaped) extending substantially straight, and is provided at its distal end with a dissecting section 220 for dissecting tissue. In addition, as shown in FIG. 2B, the dissecting device 200 has a flat shape (flattened shape as seen in vertical cross-section to a central axial direction of the dissecting device) in section. The cross-sectional shape of the dissecting device 200 is not specifically restricted; for example, the cross-sectional shape may be a crushed-circle-like shape (flattened circular shape), such as an oblong and an ellipse, a rectangle rounded at corners, or the like.

The width (the length in the major axis direction of the cross-sectional shape) W1 of the dissecting device 200 is greater than the outside diameter of the blood vessel to be harvested (in this embodiment, the great saphenous vein). To be more specific, the width W1 is preferably about 4 mm to 2 cm greater than the outside diameter of the blood vessel to be harvested. This helps ensure that the possibility of contact between the cutting device 300 and the great saphenous vein can be effectively lowered at the time of inserting the cutting device 300 into the living body along the dissecting device 200, as will be explained in the "blood vessel harvesting method" described later.

In addition, the dissecting device 200 is provided, at both ends of the major axis of the cross-sectional shape thereof, with rails 231 and 232 in the form of linear stretches of recess (or trenches/grooves) which extend in the axial direction of the dissecting device 200. Each of the rails 231 and 232 is used for connection of the dissecting device 200 with the cutting device 300, and functions as a guide section for guiding the cutting device 300. Note that the rails 231 and 232 are not limited to the linear stretches of recess (or trenches/grooves) but may be, for example, linear stretches of projection (or ridges or ribs), insofar as they each enable connection of the dissecting device 200 with the cutting device 300.

As shown in FIG. 2A, the dissecting device 200 is provided with an insertion hole 210 which opens at the proximal end and extends to a distal portion (the dissecting section 220). In this illustrated embodiment, the insertion hole 210 is a blind hole, meaning the insertion hole 210 is closed at its distal end. Into the insertion hole 210 is inserted an imaging device 400. The imaging device 400 is not specifically restricted. For example, the imaging device 400 in this embodiment, as depicted in FIG. 2A, includes or possesses an elongated main body section 410, and an illuminating section (not shown) for emitting illumination light and an imaging section 430 for imaging the front side of the dissecting device 200. The illuminating section and the imaging section 430 are disposed at a distal portion of the main body section 410. The imaging section 430 includes or possesses, for example, an objective lens system disposed at the distal portion of the main body section 410 and an imaging element (e.g., solid state image sensor such as CMOS image sensor or CCD sensor) disposed opposite to the objective lens system.

The dissecting section 220 is tapered in a narrowing manner toward the distal end of the dissecting device 200. More specifically, the distal end portion of the dissecting section 220 possesses a tapered roughly conical shape so that the length in the minor axis direction and the length in the major axis direction of the cross-sectional shape of the dissecting section 220 are both gradually decreased in a direction toward the distal end. Such a dissecting section 220 is blunt in the thickness direction, and has such a degree of sharpness (bluntness) as to be able to dissect tissues having different properties (for example, fat and skin, fat and fascia, fat and blood vessel, fat and bone, etc.) from each other without cutting branch vessels branched from the great saphenous vein. This helps ensure that a dissecting function can be sufficiently exhibited and the branch vessels are restrained from being damaged or cut by the dissecting section 220. Accordingly, bleeding can be suppressed, and the intended technique can be performed safely and smoothly. Note that the shape of the dissecting section 220 is not particularly limited insofar as it enables dissection of tissues in the thickness direction (minor axis direction) of the tissues. For example, the dissecting section 220 may be in the shape of a duck-bill such that the length in the minor axis direction of the cross-sectional shape of the dissecting section 220 is gradually decreased (tapered) toward the distal end and the cross-sectional shape at the distal end is a line segment along the major axis direction.

The dissecting section 220 is substantially colorless and transparent and is light-transmitting. This helps ensure that when the imaging device 400 is inserted into the insertion hole 210, the front side of the dissecting device 200 can be observed through the dissecting section 220 by the imaging device 400. In other words, the dissecting section 220 has the function as an observation section for observation of the inside of the living body (the great saphenous vein and its surroundings), in addition to the aforementioned function as the dissecting section. Note that the dissecting section 220 is not limited to the colorless transparent property but may be colored in red, blue, green or the like, insofar as it is light-transmitting.

The cutting device 300, at the time of moving along a great saphenous vein 1000, cuts the fat (inclusive of connective tissue) surrounding the great saphenous vein 1000 and, in addition, cuts and stanches the branch vessels branched from the great saphenous vein 1000.

The cutting device 300 is elongated plate-like in shape (plate-shaped). As shown in FIGS. 1 and 3A, the cutting device 300 has a groove portion 320 opening in a distal portion of the cutting device. The groove portion 320 possesses: a tapered blood vessel guide groove section (first groove section) 321 having a width gradually decreasing toward the proximal side; and a straight blood vessel treating groove section (second groove section) 322 which is located on the proximal side of the blood vessel guide groove section 321 and is substantially constant in width. The blood vessel guide groove section 321 is a groove section for guiding a branch vessel into the blood vessel treating groove section 322 at the time of pushing the cutting device 300 forward in a living body, and is tapered in shape for the guiding to be smoothly achieved. On the other hand, the blood vessel treating groove section 322 is a groove section for cutting and stanching the branch vessel guided to the blood vessel treating groove section 322 by the blood vessel guide groove section 321. Further, the blood vessel treating groove section 322 is provided with a treating section 330 for cutting and stanching a branch vessel.

As shown in FIG. 3A, the treating section 330 has a bipolar structure including a pair of electrodes 331 and 332 configured to generate an electric field inside the blood vessel treating groove section 322. The electrode 331 is disposed at a proximal end portion of the blood vessel treating groove section 322, while the electrode 332 is disposed on both sides with respect to the width direction of the blood vessel treating groove section 322. With a high-frequency AC voltage impressed between the electrodes 331 and 332, it is possible to heat and cut a branch vessel 1100 guided into the blood vessel treating groove section 322 and to stanch the blood vessel through thermal coagulation. A distal portion (a portion exposed to the blood vessel treating groove section 322) 331a of the electrode 331 is preferably so sharp as to be able to cut the branch vessel 1100. This helps ensure that if thermal coagulation (stanching) of the branch vessel 1100 can at least be achieved by the electric field generated between the electrodes 331 and 332, the branch vessel 1100 can be physically cut by the distal portion 331a of the electrode 331. Accordingly, the assuredness of the treatment by the treating section 330 is enhanced.

The width W2 of the blood vessel treating groove section 322 is not particularly limited but it is preferably narrower than the outside diameter of the branch vessel 1100. This helps ensure that the branch vessel 1100 can be pressed flat inside the blood vessel treating groove section 322 as shown in FIG. 3A, and, consequently, the treatment (cutting and stanching) at the treating section 330 can be performed more reliably.

The cutting device 300 is provided with a cutting edge section (cutting section) 350 for cutting the fat surrounding the great saphenous vein 1000. The cutting edge section 350 is disposed at a distal portion of the cutting device 300; in this embodiment, it is disposed along the blood vessel guide groove section 321. As will be explained also in the "blood vessel harvesting method" described later, the cutting edge section 350 has the function of cutting the fat surrounding the great saphenous vein 1000 at the time of pushing the cutting device 300 forward in the living body. Such a cutting edge section 350 preferably has such a sharpness as to be able to cut the fat without cutting the branch vessel 1100. This helps ensure that cutting of the branch vessel 1100 by the cutting edge section 350 is inhibited, so that bleeding is restrained, and the intended technique can be performed safely and smoothly.

As shown in FIG. 3B, the cutting device 300 has a pair of protection sections 341 and 342 provided on both sides with respect to the cutting device's width direction (the direction orthogonal to its moving direction). The protection sections 341 and 342 each extend along the axial direction of the cutting device 300, and their peripheral surfaces (side surfaces and distal surfaces) are rounded. As will be explained also in the "blood vessel harvesting method" described later, the protection section 341 moves along and between fat and skin while dissecting them from each other, at the time of pushing the cutting device 300 toward the distal side in a living body. Since the fat and the skin having different properties, they are rather easy to dissect from each other, even though a distal end portion of the protection section 341 is rounded, and the dissecting function of dissecting the fat and the skin from each other can be exhibited sufficiently. In addition, the rounding helps ensure that a branch vessel can be restrained from being damaged or cut by the protection section 341, and, further, damage to (cauterization of) the skin due to sliding against (friction with) the protection section 341 can be restrained. Similarly, the protection section 342 moves along and between the fat and the fascia while dissecting them from each other at the time of pushing the cutting device 300 toward the distal side in the living body. Since the fat and the fascia having different properties, they are easy to dissect from each other, even though a distal end portion of the protection section 342 is rounded, and the dissecting function of dissecting the fat and the fascia from each other can be exhibited sufficiently. Besides, the rounding helps ensure that the branch vessel can be restrained from being damaged or cut by the protection section 342, and, further, damage to (cauterization of) the fascia due to sliding against (friction with) the protection section 342 can be restrained.

As shown in FIGS. 3A and 3B, the cutting device 300 has connection sections 381, 382, 383 and 384 configured to connect with the rails 231 and 232 of the dissecting device 200. The connection sections 381 and 382 are provided at the protection section 341, and disposed on mutually opposite surface sides. Similarly, the connection sections 383 and 384 are provided at the protection section 342, and disposed on mutually opposite surface sides. These connection sections 381 to 384 are composed of stretches (lengths) of projection (or ridges or ribs) which extend in the axial direction of the cutting device 300 and correspond to the stretches of recess (trenches) of the rails 231 and 232. Since such connection sections 381 to 384 are provided, unintended detachment of the dissecting device 200 and the cutting device 300 from each other is prevented, so that the intended technique can be carried out more smoothly and accurately. Thus, in this example of the blood vessel dissecting device, both the cutting device 300 and the dissecting device 200 possess connection structure configured to connect the cutting device 300 and the dissecting device 200 to each other.

A method of harvesting or dissecting a blood vessel by use of the blood vessel dissecting device 100 possesses: a first step (blood vessel dissecting method) of dissecting the great saphenous vein 1000 in the state of being covered with surrounding fat 1200 by use of the blood vessel dissecting device 100; a second step of ligating the great saphenous vein 1000 and then cutting the great saphenous vein 1000; and a third step of extracting the great saphenous vein 1000 in the state of being covered with the surrounding fat 1200 from the living body.

First, the position of the great saphenous vein 1000 to be harvested is confirmed, and skin is incised on the basis of the position of the great saphenous vein. Next, the dissecting device 200 with the imaging device 400 inserted in the dissecting device 200 is prepared, and, while observing the inside of the living body by the imaging device 400, the dissecting device 200 is inserted from the incision 1300 into the living body along the great saphenous vein 1000 while keeping the dissecting device 200 spaced from the great saphenous vein 1000. Then, as shown in FIG. 4A, the dissecting device 200 is disposed on the upper side (the skin 1400 side) of the great saphenous vein 1000. In this case, the dissecting device 200 is so disposed that the thickness direction of the dissecting device 200 agrees substantially with the aligning direction in which the dissecting device 200 and the great saphenous vein 1000 are aligned. In this operation, the dissecting device 200 is inserted between the fat 1200 and the skin 1400 (between the tissues having different properties), and the skin 1400 and the fat 1200 are dissected from each other in the thickness direction of the dissecting device 200 (in the aligning direction in which the dissecting device 200 and the great saphenous vein 1000 are aligned). Such an area is an area where dissection can be achieved particularly easily, so that this operation can be carried out more smoothly and accurately. The dissecting device 200 thus dissects tissue in a direction along the longitudinal extent of the vein.

Subsequently, the cutting device 300 is prepared, and the connection section 381 is connected to the rail 231 of the dissecting device 200. Then, the state of the cutting device 200 is aligned on the upper side of the great saphenous vein 1000, the cutting device 300 is inserted into and moved in the living body while guiding the cutting device 300 with the dissecting device 200 as shown in FIG. 4B. In this case, the cutting device 300 is moved forward while dissecting the skin 1400 from the fat 1200 by the protection section 341, and while dissecting the fascia 1500 from the fat 1200 by the protection section 342. Furthermore, the cutting device 300 cuts the fat 1200 present on the one lateral side of the great saphenous vein 1000 by the cutting edge section 350 in the left-right direction (in the aligning direction in which the cutting device 300 and the great saphenous vein 1000 are aligned), and, concurrently, cuts and stanches the branch vessel 1100 by the treating section 330.

Here, since the width W1 of the dissecting device 200 is greater than the outside diameter of the great saphenous vein 1000 as aforementioned, the cutting device 300 can be pushed forward along the great saphenous vein 1000 while keeping the cutting device 300 laterally spaced from the great saphenous vein 1000, as shown in FIG. 4B, so that the great saphenous vein 1000 can be prevented from being damaged during this operation. In addition, since the protection sections 341 and 342 are rounded, the possibility of damaging the skin 1400 or the fascia 1500 by contact with the cutting device 300 is lowered.

Next, the cutting device 300 is drawn out, and the connection section 382 of the cutting device 300 thus drawn out is connected to the rail 232 of the dissecting device 200. Then, the cutting device 300 is inserted again into the living body while guiding the cutting device 300 with the dissecting device 200, to dispose the cutting device 300 on the other lateral side of the great saphenous vein 1000, as shown in FIG. 5A.

Subsequently, the dissecting device 200 is drawn out, and the rail 232 of the dissecting device 200 thus drawn out is connected to the connection section 384 of the cutting device 300. Then, the dissecting device 200 is inserted again into the living body while guiding the dissecting device 200 with the cutting device 300, to dispose the dissecting device 200 on the lower side (the fascia 1500 side (bone side)) of the great saphenous vein 1000, as shown in FIG. 5B. In this operation, the dissecting device 200 is inserted between the fat 1200 and the fascia 1500 (inserted into the boundary between the tissues having different properties), and the fat 1200 and the fascia 1500 are dissected from each other in the thickness direction of the dissecting device 200. Such an area is an area where dissection can be particularly easily achieved, so that this operation can be carried out more smoothly and accurately.

By the above-mentioned operations, the fat 1200 surrounding the great saphenous vein 1000 is dissected over the entire perimeter of the vein, and the great saphenous vein 1000 is dissected in the state of being covered with the surrounding fat 1200. The thickness of the fat 1200 dissected together with the great saphenous vein 1000 and located in the surroundings of the great saphenous vein 1000 is not particularly limited. It is preferable, however, that the thickness is about 0.1 mm to 10 mm, more preferably about 1 mm to 8 mm, and further preferably about 3 mm to 5 mm.

Next, both ends of that part of the great saphenous vein 1000 which is to be harvested are ligated and then cut.

Subsequently, the great saphenous vein 1000 is extracted in the state of being covered with the surrounding fat 1200, to the outside of the living body via the incision 1300.

By the first to third steps as above-mentioned, the great saphenous vein 1000 can be harvested while the great saphenous vein is in the state of being covered with the surrounding fat 1200. In such a method, while using the dissecting device 200 for treating a part which is rather easy to dissect so as to reduce such damages as bleeding and while using the cutting device 300 for treating the fat which is difficult to dissect, the great saphenous vein 1000 can be harvested smoothly and with low invasion. In addition, since the first step can be carried out without cutting the great saphenous vein 1000, blood can be kept flowing through the great saphenous vein 1000 for a time as long as possible. Accordingly, the great saphenous vein 1000 is placed in an ischemic state for a shortened period of time, so that the great saphenous vein 1000 can be harvested with less damage.

Here, a great saphenous vein 1000 covered with fat 1200 constitutes a bypass vessel having a superior long-term patency rate, as compared with a great saphenous vein 1000 not covered with fat 1200. The reason is considered as follows. While the great saphenous vein 1000 is used as an artery bypass vessel, arteries are generally higher than veins in the blood pressure (the internal pressure exerted thereon by blood). When a great saphenous vein in an exposed state of being not covered with tissue is used as a bypass vessel, therefore, the great saphenous vein cannot endure the blood pressure and is therefore expanded by the blood pressure, resulting in lowered blood flow. In addition, thickening of blood vessel wall occurs in the process of remodeling (structural alteration) or in the process of recovery from damage to tissue. Such thickening of blood vessel wall is considered to influence the development of arterial sclerosis. From such a cause, the use of a great saphenous vein in the exposed state of being not covered with tissue as a bypass vessel would, in the long run, lead to vascular occlusion.

On the other hand, where the great saphenous vein 1000 is covered with fat 1200, expansion of the great saphenous vein 1000 is restrained by the fat 1200, and bending and the like of the great saphenous vein 1000 are also restrained. Therefore, the lowering in blood flow as above-mentioned can be inhibited. In addition, the covering with the fat 1200 reduces damages to the great saphenous vein 1000, specifically, damages to endotheliocytes, smooth muscles, nutrient vessels (capillary plexus), etc. Therefore, the aforementioned thickening of blood vessel walls can be restrained. For these reasons, the use of the great saphenous vein 1000 covered with the fat 1200 as a bypass vessel enables an excellent long-term patency rate. Especially, in this embodiment, nutrient vessels are left at the blood vessel walls of the great saphenous vein 1000 and in the fat 1200. For this reason, nutrients are supplied to the great saphenous vein 1000 serving as the bypass vessel, even after the bypass grafting. This is considered to be the reason why the aforementioned effect is enhanced.

While this embodiment has been described, the configuration of the blood vessel dissecting device 100 is not limited to the configuration in this embodiment. For example, the rails 231 and 232 may be omitted from the dissecting device 200, and the connection sections 381 to 384 may be omitted from the cutting device 300. In this case, for example, it may be sufficient to insert the cutting device 300 into a living body along the dissecting device 200 which is inserted into the living body earlier. Alternatively, it may be sufficient to insert the dissecting device 200 into a living body along the cutting device 300 which is inserted into the living body earlier.

The cutting device 300 is not specifically restricted insofar as it can cut the fat 1200. For instance, a configuration may be adopted in which the fat 1200 is cut by something like a pair of scissors.

The blood vessel dissecting method is not limited to the procedure adopted in this embodiment. For instance, the order of insertion of the dissecting device 200 and the cutting device 300 is not specifically restricted, and any of left, right, upper and lower portions of the great saphenous vein 1000 may be dissected first. For instance, a procedure may be adopted in which, first, upper and lower sides of the great saphenous vein 1000 are dissected by use of the dissecting device 200, and, then, left and right sides of the great saphenous vein 1000 are dissected by use of the cutting device 300. On the other hand, left and right sides of the great saphenous vein 1000 may first be dissected by use of the cutting device 300, and, then, upper and lower sides of the great saphenous vein 1000 may be dissected by use of the dissecting device 200.

While one dissecting device 200 and one cutting device 300 are used in this embodiment, two dissecting devices 200 and two cutting devices 300 may be used. In this case, for example, a procedure may be adopted wherein, first, a first dissecting device 200 is disposed on the upper side of the great saphenous vein 1000, next a first cutting device 300 is disposed on one of left and right sides of the great saphenous vein 1000, then a second cutting device 300 is disposed on the other of the left and right sides of the great saphenous vein 1000, and a second dissecting device 200 is disposed on the lower side of the great saphenous vein 1000. Such a procedure eliminates the need to draw out the dissecting device 200 and the cutting device 300 in the course of the procedure, so that the aforementioned procedure can be carried out smoothly.

While the dissecting device 200 is inserted between the fat 1200 and the skin 1400 and between the fat 1200 and the fascia 1500 in this embodiment, the insertion position of the dissecting device 200 is not particularly limited. For instance, the dissecting device 200 may be inserted between tissues having different properties, such as between the fat 1200 and a blood vessel (other than the great saphenous vein 1000), between the fat 1200 and a bone, between the fascia 1500 and a bone, or the like. Further, the insertion between tissues having different properties (insertion into the boundary between tissues having different properties, insertion into tissue between tissues having different properties, or the like) is not restrictive; for example, the dissecting device 200 may be inserted into the fat 1200, thereby dissecting the fat 1200.

While fat is cut by the cutting device 300 in this embodiment, the tissue to be cut by the cutting device 300 is not limited to fat. For instance, tissue between a skin-fat boundary and a fat-muscle boundary, tissue between a skin-fat boundary and a fat-interosseous membrane boundary, connective tissue, tissue between a skin layer and a muscle layer, tissue between a skin layer and an interosseous membrane, branch vessels, and the like may also be cut by the cutting device 300.

In this embodiment, the dissecting device 200 is disposed spaced from the great saphenous vein 1000 so as not to contact the great saphenous vein 1000. But the dissecting device 200 may be disposed in contact with the great saphenous vein 1000. In other words, the dissecting device 200 may be inserted between the great saphenous vein 1000 and the fat 1200.

FIG. 6 illustrates another embodiment of a vein dissecting or harvesting device. This embodiment of the vein dissecting device 500 includes or possesses a dissecting member 508 which incorporates a cutting member 518. The vein dissecting device 500 also includes or possesses an elongated hollow member 502 projecting rearwardly (in the proximal direction) from the dissecting member 508. The elongated hollow member 502 possesses a proximal end portion 504 and a distal end portion 506, and the dissecting member 508 is mounted on or fixed to the distal end portion 506 of the elongated hollow member 502.

Figure 7B:
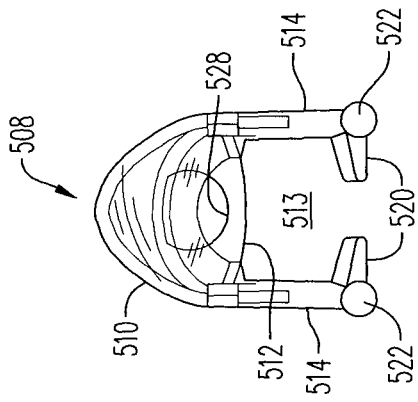
FIG. 7B is a front view of the dissecting member forming a part of the dissecting device illustrated in FIG. 6.

FIGS. 7A-7D depict the dissecting member 508 in more detail. Those figures illustrate that the dissecting member 508 possesses a mount 512 that may be generally tubular in configuration. By way of this mount 512, the dissecting member 508 is mounted on the distal end portion 506 of the elongated hollow member 502. This can be accomplished by, for example, welding, adhesive, fitting together, etc. Projecting from the mount 512 are two spaced-apart side portions or side walls 514. In the illustrated embodiment, these side portions 514 project vertically downwardly away from the mount 512 as best illustrated in FIG. 7B. The dissecting member 508 also includes or possesses holding portions 520, each of which projects inwardly from one of the side portions 514. In the illustrated embodiment, the holding portions 520 are horizontally oriented and project inwardly towards one another as generally illustrated in FIG. 7B. The holding portions 520 are preferably configured and arranged to retain dissected tissue and/or the vein.

Figure 9:
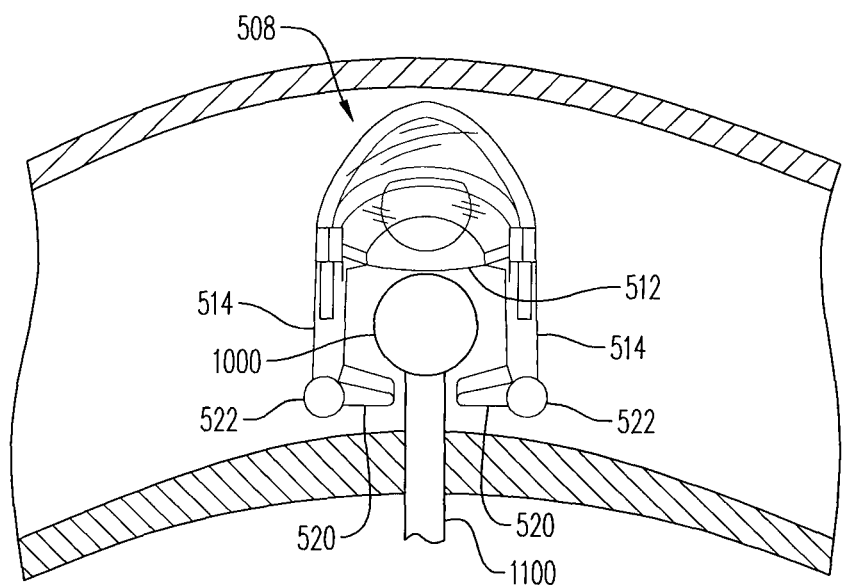
FIG. 9 is a front view of the dissecting member shown in FIG. 8A showing the way in which the dissecting member interacts with the vein and a side branch of the vein during use of the dissecting device.

The mount 512 defines a top portion which, together with the two spaced-apart side portions 514 and the two holding portions 520, defines a space or region 513. As described in more detail below, this region 513 represents a vein-receiving region or space configured to receive the vein (e.g., saphenous vein) during use and operation of the dissecting device 500. An example of this is shown in FIG. 9 which schematically illustrates the dissecting member 508 during use. As the dissecting member 508 is moved along the vein 1000 during use, the vein 1000 is received or positioned in the vein-receiving region or space 513 defined between the holding portions 520, the side portions or side members 514 and a part of the mount 512 forming an upper confine.

Figure 7C:
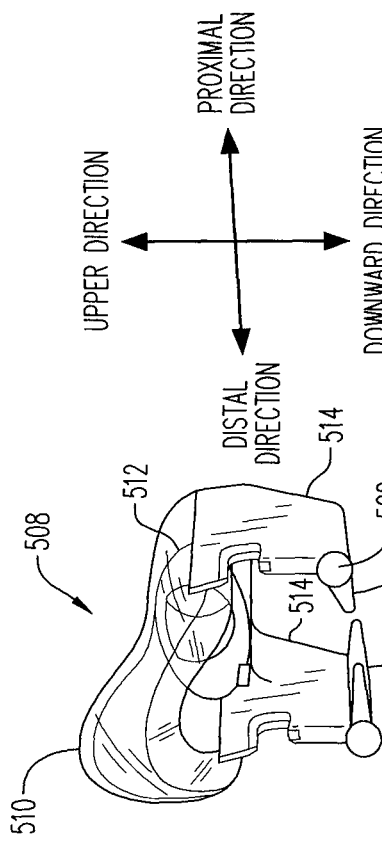
FIG. 7C is a front perspective view of the dissecting member forming a part of the dissecting device illustrated in FIG. 6.
Figure 7A:
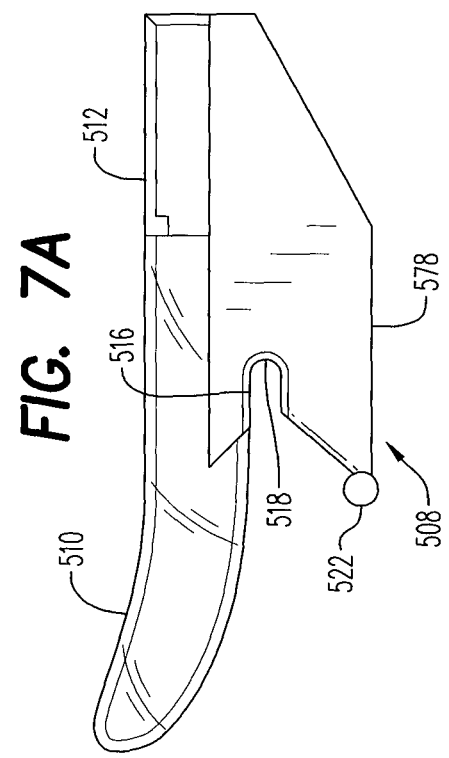
FIG. 7A is a side view of the dissecting member forming a part of the dissecting device illustrated in FIG. 6.
Figure 7D:
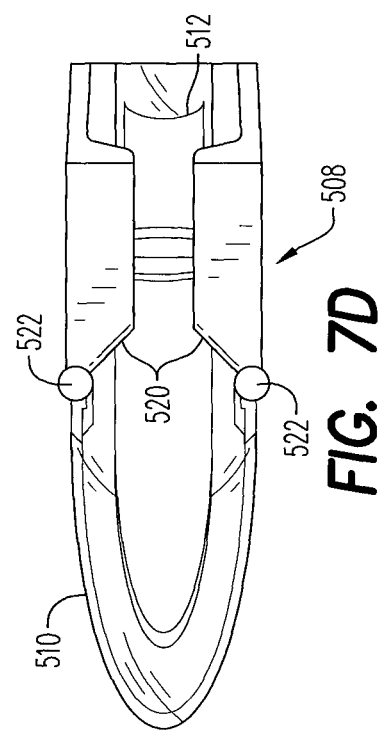
FIG. 7D is a bottom view of the dissecting member forming a part of the dissecting device illustrated in FIG. 6.

As best illustrated in FIGS. 7A and 7C, the distal end portion 510 of the dissecting member 508 is configured as an upturned member. According to one embodiment as illustrated, the upturned member 510 may be in the form of an upwardly curved member that is curved along at least its distal end portion of its extent in an upward direction. The upturned distal end portion 510 of the dissecting member 508 constitutes an upwardly curved protrusion member. FIG. 11 shows that the upturned or curved distal end portion 510 of the dissecting member 508 can be configured to possess the distal end portion that is upwardly curved and a proximal portion 517 that is linear or straight. As will be explained in more detail below, the upturned or upwardly curved distal end portion 510 is configured to curve away from the vein during use of the dissecting device 500. The upturned or upwardly curved distal end portion 510 is preferably made of transparent material. This can help facilitate viewing a position of the vein with a viewing device and facilitate moving the viewing device along the vein.

Each of the side members 514 includes or possesses a groove 516 that is open at one end (i.e., the forward or distal end on the left as illustrated in FIG. 7A) and closed at the opposite end. At the closed end, the groove terminates in a curved section representing a cutting member 518. The grooves 516 and the cutting members 518 are preferable configured in a way that facilitates cutting of, for example, side branches of the vein. That is, side branches projecting from the vein, such as the side branches 1100 shown in FIGS. 4A, 4B, 5A and 5B, can be captured and guided in the grooves 516 and cut by the cutting member 518. To facilitate cutting, the cutting members 518 can be sharpened or otherwise provided with a cutting edge.

The dissecting member 508 also possesses several projections 522. Each projection 522 is positioned at the front surface or front side of one of the side portions 514, generally at a position where each side portion 514 intersects the respective holding portion 520 as best illustrated in FIG. 7B.

The projections 522 help facilitate smooth insertion of the dissecting device 508 into the living body and relatively smooth movement of the dissecting device along the vein (e.g., saphenous vein) during the dissecting operation. As described in more detail below, the method of use or operation can involve initially contacting the distal end portion of the dissecting member and the projections 522 of the dissecting member on a living body while the dissecting device is inclined to the body, and then inserting the distal end portion of the dissecting member into the body after puncturing or sticking the body with the projection and inserting the projection into the living body.

The projections 522 are preferably positioned so that they are located superior to (i.e., vertically above) the bottom surface of the dissecting device (e.g., the bottom surface of the holding portions 520). The projections 522 are preferably located superior to the bottom surface of the dissecting device in FIG. 8B.

Figure 8A:
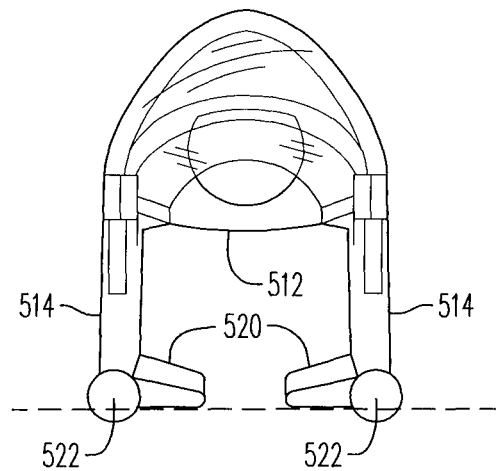
FIG. 8A is a front view of the dissecting member forming a part of the dissecting device illustrated in FIG. 6 illustrating the positioning of the projections relative to the bottom surface of the dissecting member.
Figure 8B:
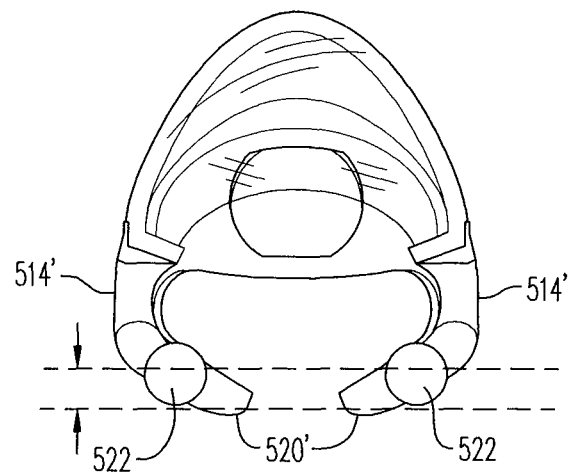
FIG. 8B is a front view of another embodiment of the dissecting member forming a part of the dissecting device illustrated in FIG. 6.

In the embodiment of the dissecting member 508 illustrated in FIGS. 7A-7D and FIG. 8A, the side portions or side members 514 are straight vertically oriented members, the holding portions 520 are straight horizontally oriented members, and the holding portions 520 are perpendicular to the respective side portions 514. The dissecting member 508 is not limited to this particular configuration. FIG. 8B shows an alternative configuration of the dissecting member in which the side portions or side members 514' are curved generally inwardly towards one another and the holding portions 520' are curved generally inwardly towards one another. It is also possible to implement other configurations, such as one in which the side portions are straight and the holding portions are curved, and another one in which the side portions are curved and the holding portions are straight.

The dissecting member 508 may be configured such that the mount 512, the side portions 514, the holding portions 520, the projections 522 and the upturned distal end portion 510 are formed as an integrated and unitary part.

Figure 10C:
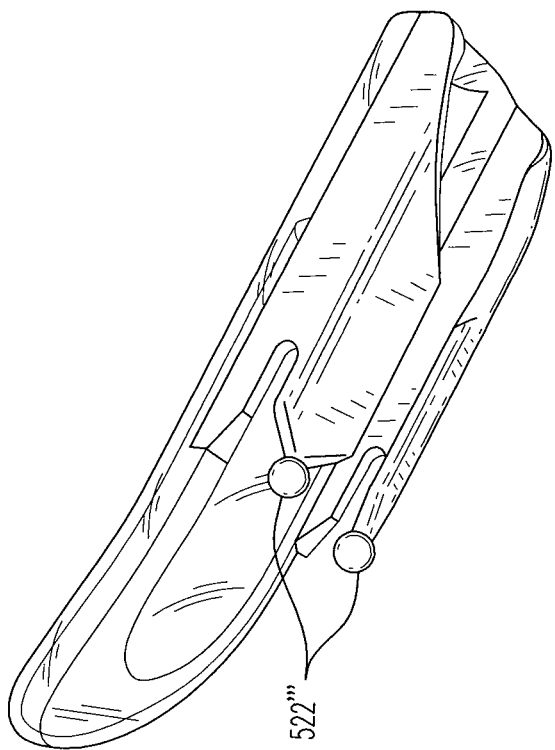
FIGS. 10A-10C are bottom perspective views of different embodiments of the dissecting member each possessing differently configured projections.
Figure 10B:
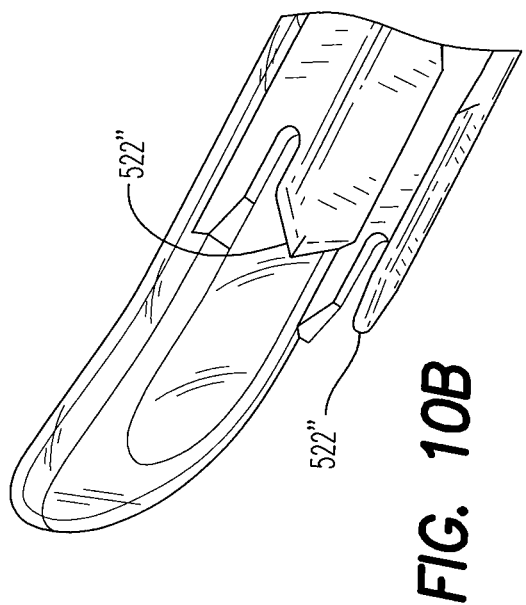
Figure 10A:
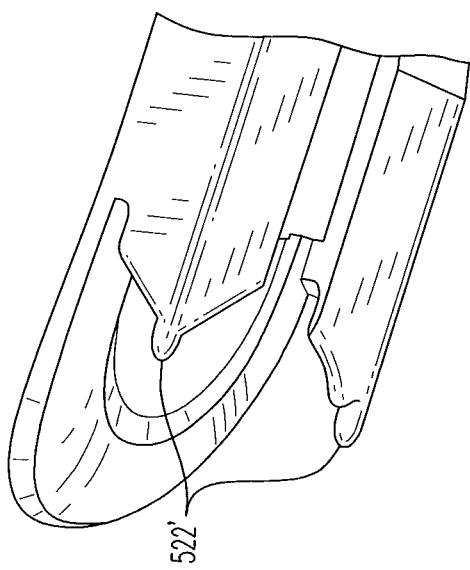

The embodiment of the dissecting member 508 shown in FIGS. 7A-7D includes or possesses projections 522 in the form of spherical members positioned at the intersection of the side portion and the holding portion. The projections are not limited to this configuration and positioning. FIGS. 10A-10C illustrate several other embodiments of the projections. In these different embodiments, the projections are differently configured and arranged relative to the version shown in FIGS. 7A-7D. In FIG. 10A, the projections 522' are configured as cone-shaped or bullet-shaped projections at the corner where the side portion 514 meets or intersects the holding portion 520. The projection 522" in FIG. 10B is formed by a tapering part of the holding portion 520 at which the front edge of the holding portion tapers to a rounded point at the midpoint of the holding portion 520. The embodiment of the projection 522''' in FIG. 10C is similar to FIG. 10B, but additionally includes or possesses the spherically shaped projection at the tapered midpoint of the holding portions. The pointed nature of the projections shown in FIGS. 10 A and 10B facilitate dissecting and sticking the tissue.

Figure 11A:
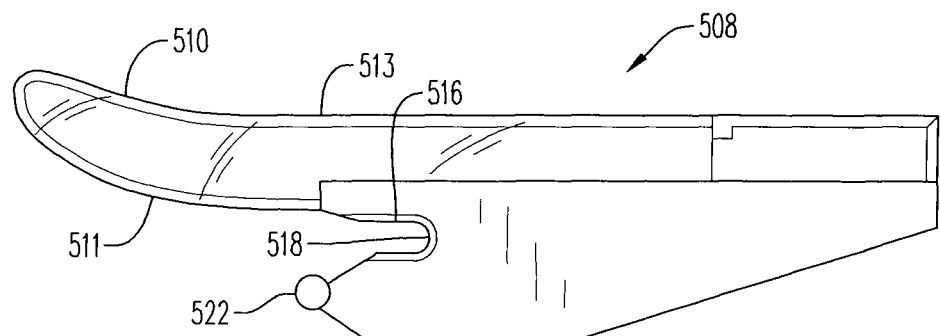
FIG. 11A is an enlarged side view of the dissecting member illustrating the relative positions of different parts of the dissecting member.

As generally illustrated in FIG. 11, it is preferable that the projections 522 be positioned so that the entirety of the groove 516 in each of the side portions 514 is located posterior to the projection 522 (i.e., behind, proximal to or to the right of the projection 522 in FIG. 11). Stated differently, the projection 522 on each of the side portions or side members 514 is positioned in front of or on the distal side of the groove 516 (i.e., to the left of the groove in FIG. 11). The groove 516 on each of the side portions 514 is also preferably located posterior to (i.e., below) the upturned distal end portion 510 of the dissecting member 508 as also illustrated in FIG. 11. The groove 516 in each of the side portions 514 is positioned superior to or above the projections 522 as also depicted in FIG. 11A. FIG. 11A also shows that the projections 522 are positioned posterior to (i.e., behind or proximal to) the upturned distal end portion 510 of the dissecting member 508. The projections 522 on each of the side portions 514 are also located under or below the bottom surface 511 of the upturned distal end portion 510.

A method of using the dissecting device 500 shown in FIGS. 6, 7A-7D, 8A and 8B to harvest or dissect a blood vessel (e.g., a vein such as a saphenous vein) may be generally similar to the method described above. That is, the method may involve using the dissecting device 500 to dissect the blood vessel in a condition in which the blood vessel is covered with surrounding fat (e.g., some of the fat 1200 shown in FIGS. 4A, 4B, 5A and 5B), ligating and cutting the blood vessel, and then removing the severed or dissected blood vessel in a condition in which the blood vessel is covered with surrounding fat from the living body. More specifically, the position of the blood vessel to be dissected or harvested (e.g., great saphenous vein 1000 shown in FIGS. 4A, 4B, 5A and 5B) to be harvested is identified or confirmed, and an incision is then made in the living body (e.g., leg of a patient) to provide an access site to the vein (saphenous vein) as well as the saphenous fascia surrounding the vein. The living body is incised based on the confirmed or determined position of the blood vessel. Holding the elongated member 502 of the dissecting device 500 (or another operating member connected to the elongated member 502), the user may then insert the dissecting member 508 of the dissecting device 500 into the living body by way of the incision. The dissecting member 508 is then manipulated or moved to generally position the dissecting member 508 relative to the vein 1000 in the manner illustrated in FIG. 9. In this position, the vein 1000 is located in the region or area 513 surrounded by the holding portions 520, the side portions 514 and the top portion defined by the mount 512. FIG. 9 illustrates the positioning of the dissecting member 508 from the front (i.e., as viewed along the vein 1000).

Figure 12:
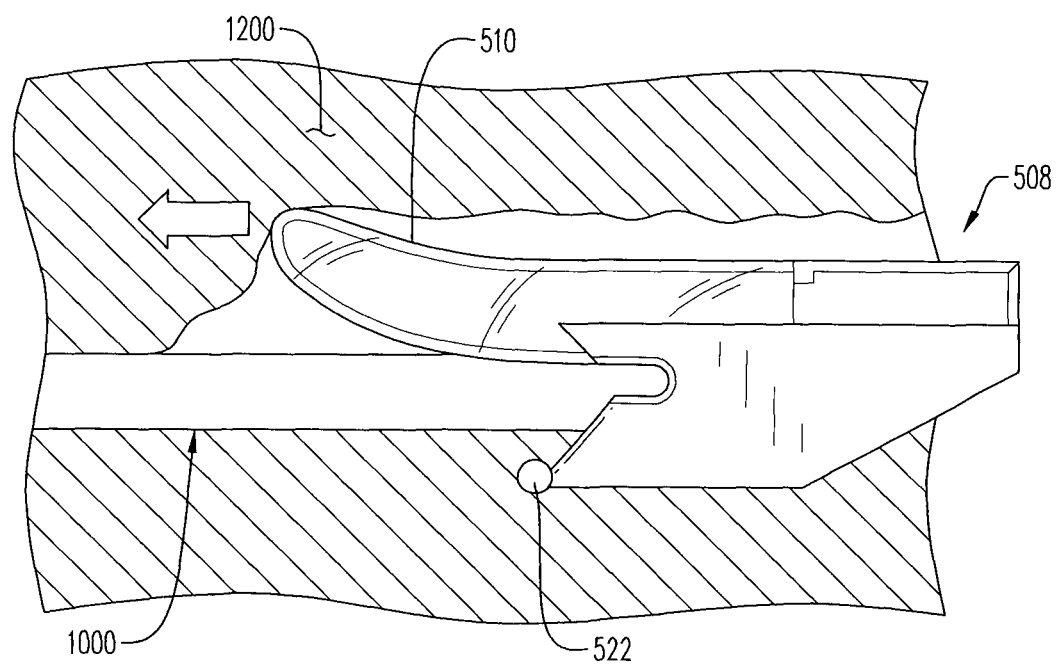
FIG. 12 is an enlarged side view of the dissecting member illustrating the manner in which the dissecting member dissects the vein during use of the dissecting device.

FIG. 12 illustrates the dissecting member 508 from the side as the dissecting member 508 is moved along the vein 1000. FIG. 12 illustrates that as the dissecting member 508 is moved along the vein 1000 in the forward or distal direction indicated by the arrow (i.e., to the left in FIG. 12) the upturned member 510 constituting the distal end portion of the dissecting member lifts and separates fat tissue 1200 from the vein 1000. The fat tissue is peeled away in much the same way as an adhesive sticker is peeled off its backing. This peeling result is illustrated in FIG. 12. By virtue of the curved or upturned distal end portion 510 of the dissecting member 508, potentially damaging contact between the distal end portion of the dissecting member and the vein 1000 is reduced. The curved or upturned member 510 thus advantageously helps to avoid injury to the vein 1000. If the distal end portion of the dissecting member was configured as a straight distal end portion (i.e., no curved configuration), it would be more likely for the distal end portion of the dissecting member to contact the vein, for example by virtue of the distal-most end of the dissecting member poking or sticking the vein. The upturned distal end portion 510 of the dissecting member facilitates dissection or separation of the tissue from the vein. The upturned member possesses only a limited circumferential extent (i.e., the upturned distal end portion 510 does not extend 360°). The method of use or operation can thus involve forward moving the dissecting member for a relatively short distance, rotating the dissecting device to dissect a circumferential region, forward moving the dissecting device so that the upturned member helps dissects a different circumferential region, forward moving the dissecting device, etc.

As the dissecting member 508 moves along the vein 1000, the dissecting device may encounter side branches of the vein 1000. Examples of such side branches are shown in FIGS. 4A, 4B, 5A, 5B and identified as 1100. By appropriately aligning the side branch 1100 with the groove 516 in one of the side portions 514, the side branch may enter the groove 516 as the dissecting member 508 is moved forward and will be cut by the cutting member 518.

After the dissecting member 508 is advanced along the entire longitudinal extent of the vein 1000 that is to be dissected or removed, the dissecting member 508 is moved in the rearward or proximal direction (i.e., to the right in FIG. 12). The dissecting member 508 can then be rotated, for example, by ninety (90) degrees, and then once again inserted into the living body to dissect the tissue surrounding the vein 1000 (i.e., the fat 1200) from the vein 1000 at circumferential location different from the dissection performed by the first pass of the dissecting member 508 along the vein 1000. This procedure can be repeated as many times as necessary to dissect the tissue from the vein so that the vein (and tissue surrounding the vein) is separated from adjacent tissue. It may be necessary to perform several passes of the dissecting member 508 as described. With the dissecting member 508 preferably removed from the living body, the ends of the dissected vein are then ligated and cut, and the severed vein is then removed from the living body.

Figure 11B:
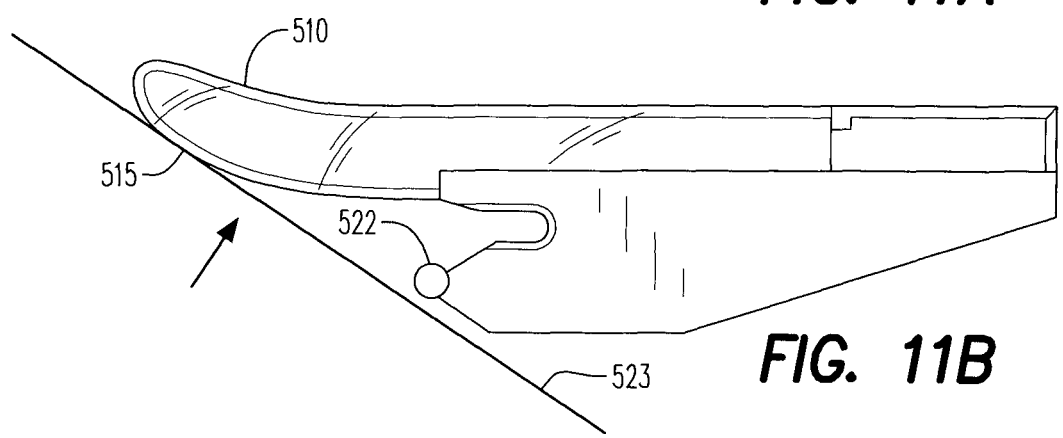
FIG. 11B is an enlarged side view of the dissecting member illustrating the relative positions of different parts of the dissecting member.

To further facilitate the smooth introduction of the dissecting member 508 into the living body and movement of the dissecting member 508 along the vein, the projections 522 are preferably positioned relative to the upturned or curved distal end portion 510 of the dissecting member 508 so that the projections 522 are located posterior to (rearward of or proximal to) a tangent to the bottom surface of the upturned or curved distal end portion 510 of the dissecting member 510 as illustrated in FIG. 11B. In the embodiment shown in FIG. 11B, the bottom surface of the upturned member 510 constituting the distal end portion of the dissecting member possesses a flat region 515, and the tangent line 523 represents a continuation of this flat bottom surface portion 515 of the upturned member 510. The upturned member 510 is preferably configured so that when the flat bottom surface portion 515 of the upturned member 510 contacts a surface of the body, the projections 522 don't contact the surface of the body. That is, when the flat bottom surface portion 515 of the upturned member 510 contacts a surface of the body, the tangent line 523 is under the projections. If the bottom surface of the upturned or curved distal end portion 510 of the dissecting member 508 is curved along its entire extent (i.e., there is no flat bottom surface portion 515), the projections 522 are preferably positioned behind or proximal to a tangent line anywhere along the curved bottom surface.

One benefit associated with the above-described positioning of the projections 522 relative to the tangent arises during insertion of the dissecting member into the living body. If the projections 522 are positioned in front of the line or tangent 523, when the dissecting member is inserted into the living body by way of the incision in the skin, the projections 522 may tend to contact (poke or stick) and possibly damage the vein (tissue) before the upturned distal end portion 510 of the dissecting member 508 has an opportunity to begin the desired peeling back of the tissue and vein dissection shown in FIG. 12. In such a case, it may be difficult to change the direction of movement of the dissecting member 508 as is typically desired because the direction of movement of the dissecting device during insertion through the skin incision is different than the movement of the dissecting member along the vein during the dissection operation.

FIGS. 13-15 illustrate additional aspects of the upturned or upwardly curved distal end portion 510 of the dissecting member 508. As illustrated in FIGS. 13 and 14, the upturned or curved distal end portion 510 of the dissecting member 508 possesses a frame portion 524 that surrounds a through opening or through hole defining a window 526. As illustrated in FIG. 14, as seen from the bottom, the frame portion 524 exhibits a curvilinearly tapered shape (bullet shape). The benefit associated with configuring the upturned or curved distal end portion 510 of the dissecting member 508 as a frame portion surrounding the through window 526 is that there is less surface contact between the bottom surface of the upturned distal end portion 510 of the dissecting member 508 and the tissue (fat) as the dissecting member 508 is being moved in the living body along the vein. That is, the surface area of the distal end portion 510 in contact with the vein or other tissue is reduced by virtue of the existence of the window 526. It is thus easier to move the dissecting member through the living body along the vein.

Figure 16A:
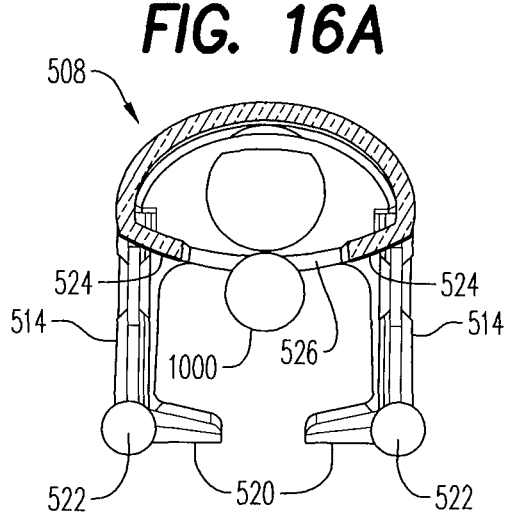
FIG. 16A is a front view of the dissecting member illustrating the way in which the dissecting member, by virtue of the window, interacts with the vein being dissected.
Figure 16B:
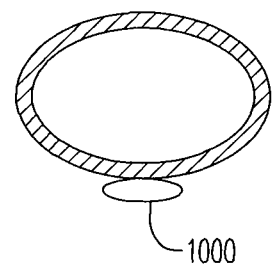
FIG. 16B is a front view of a manner of interaction between a dissecting member without a window and a vein being dissected.

There is also another benefit associated with configuring the upturned distal end portion 510 distal end portion of the dissecting member as a frame member that surrounds a through window 526. This additional benefit is illustrated in FIGS. 16A and 16B. FIG. 16A illustrates the frame portion 524 of the upwardly curved distal end portion 510 of the dissecting member 508 and shows the way in which the vein 1000 is able to be positioned in the window 526 surrounded by the frame portion 524. FIG. 16B illustrates that if the distal end portion did not include or possess the through opening defining the window, the distal end portion of the dissecting member would contact and press against the vein 1000, thus possibly damaging the vein.

As described above, the elongated member 502 projecting proximally from the dissecting member 508 is a hollow elongated member, meaning the hollow elongated member possesses a lumen 528. This lumen 528 is illustrated by way of example in FIG. 15. This lumen 528 opens into the dissecting member 508, particularly the area or space 513 surrounded by the side portions 514, the holding portions 520 and the part of the mount 512 spanning the side portions 514. During use of the dissecting device 500, it is possible to introduce a viewing device or imaging device (e.g., an endoscope, camera, etc.) into the lumen 528 and advance the viewing device along the lumen 528 to the distal open end of the lumen 528. This viewing device can then be used to view a viewing area generally in front of the dissecting member 508 as the dissecting member is being moved in the living body along the vein 1000. An example of a viewing device 1002 is schematically illustrated in FIG. 15.

Figure 17A:
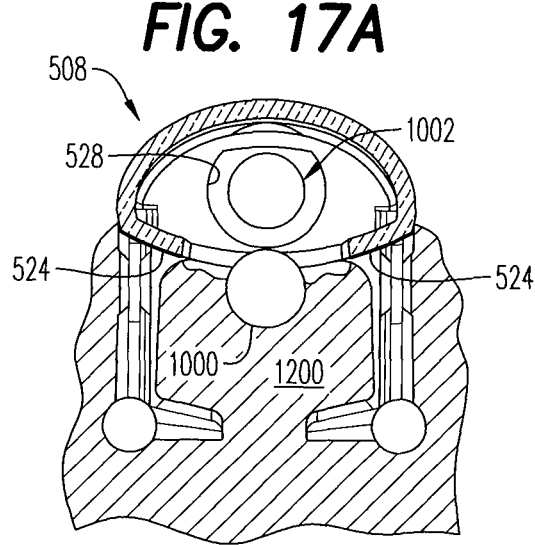
FIG. 17A is a front view of the dissecting member illustrating the way in which the dissecting member and viewing member, by virtue of the window, interacts with the vein being dissected.
Figure 17B:
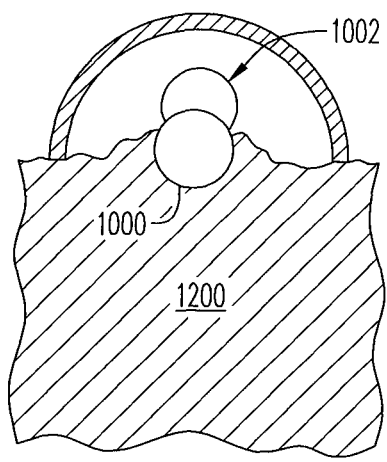
FIG. 17B is a front view of a dissecting member without a window illustrating the way in which the dissecting member and the viewing member interact with the vein being dissected.

FIGS. 17A and 17B illustrate another benefit associated with configuring the distal end portion or upturned member as a frame portion surrounding a window. The frame portion tends to hold the tissue (fat) 1200 surrounding the vein 1000 so that the tissue may not interfere with the field of view of the viewing device 1002 located in the lumen 528 of the hollow elongated member. On the other hand, as illustrated in FIG. 17B, in the absence of the frame portion, the tissue is free to force its way upward together with the vein 1000 into the field of view of the viewing device 1002, a result that is not preferable.

A part of the upturned distal end portion 508 of the dissecting member or the entirety of the upturned distal end portion 508 of the dissecting member may be made transparent, for example buy being made of transparent material. A holding portion side of the dissecting member's distal end portion may have a concave shape as the window. The width of the holding portion is thicker or greater than the width of the dissecting member.

Figure 18A:
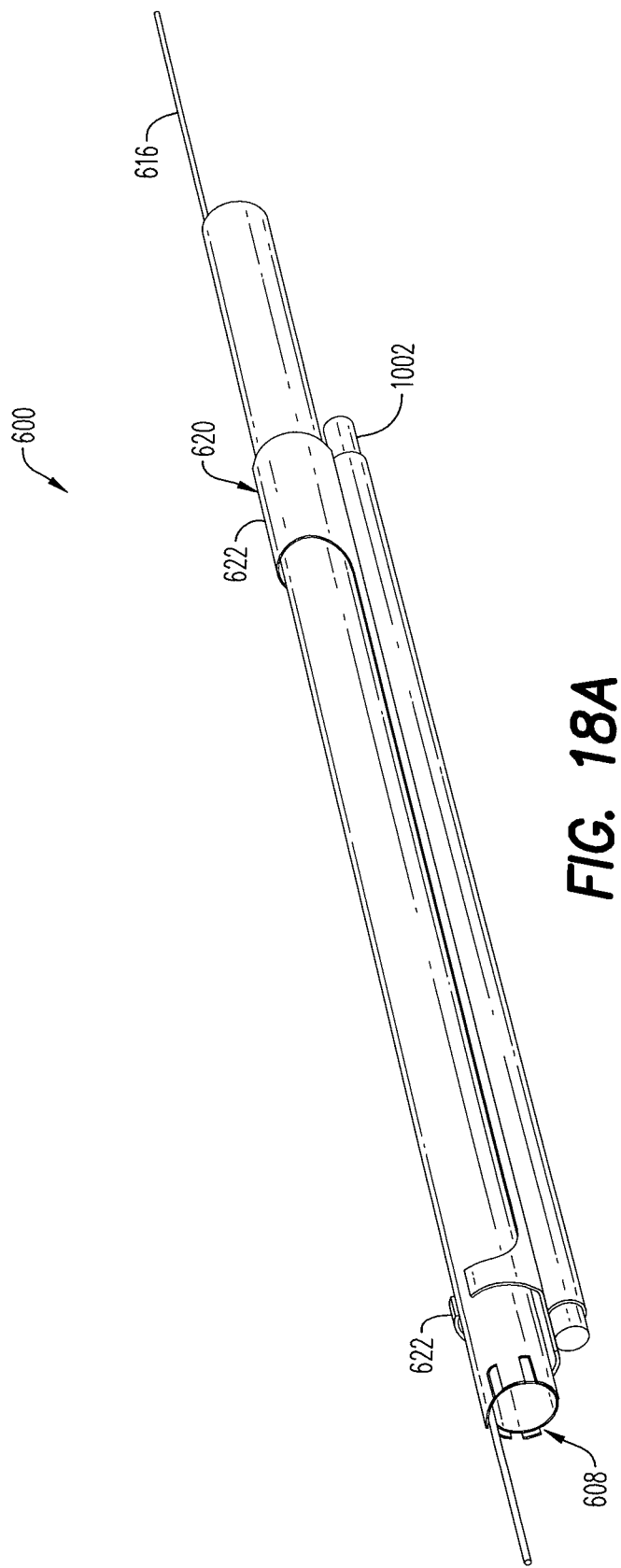
FIGS. 18A and 18B are perspective and exploded views respectively of another embodiment of the dissecting device.
Figure 18B:
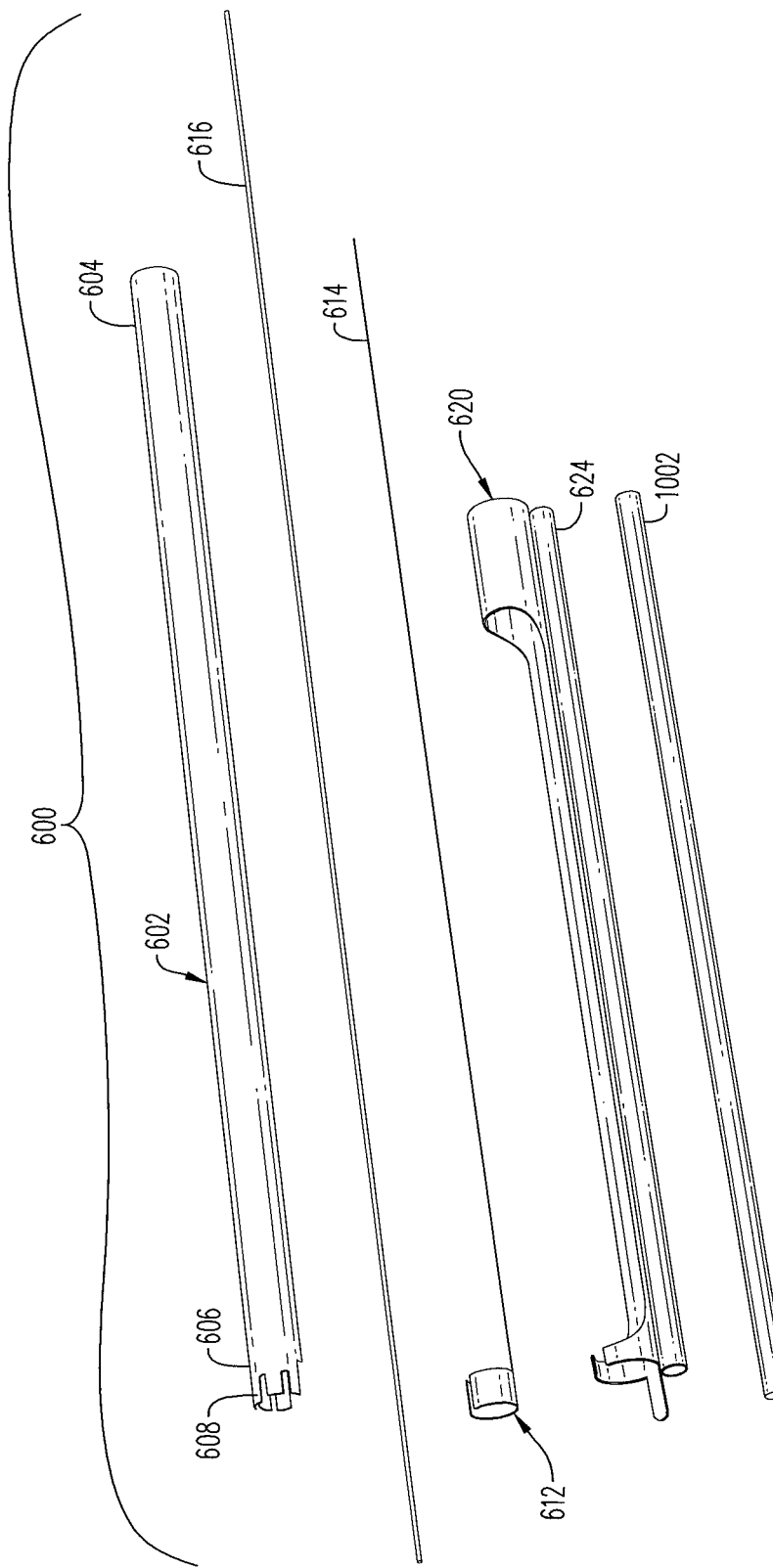

FIGS. 18A and 18B illustrate another embodiment of the dissecting device. This embodiment of the dissecting device 600 includes or possesses an elongated dissecting member 602 possessing a generally cylindrical shape and hollow configuration. The elongated cylindrically-shaped dissecting member 602 possesses a proximal end portion 604 and a distal end portion 606. A protrusion 608 is positioned at the distal end portion 606 of the dissecting member 602. In the illustrated embodiment, the protrusion 608 is comprised of a series of circumferentially spaced apart and axially extending protrusions 608 that alternate with circumferentially spaced apart and axially extending grooves. The protrusion member (alternating protrusions 608 and grooves) is an integral part of the dissecting member 602. That is, the protrusion 608 is integrally formed in one piece as a unitary part of the dissecting member 602.

The protrusion 608 at the distal end of the dissecting member 602 thus causes the distal end of the dissecting member 602 to exhibit an annular saw tooth-shaped profile as generally illustrated in FIG. 18B. Stated differently, the distal end of the dissecting member 602 possesses a series of circumferentially spaced apart axially extending notches or indents that define an annular saw tooth-shaped configuration as illustrated.

The protrusions 608 are each preferably shaped so that they possess a curved shape as seen from the end (the distal end or left end in FIG. 18B). For example, the curvature (radius of curvature) of the protrusions member 608 can be similar to the curvature (radius of curvature) of the outer surface of the dissecting member 602. In addition, the protrusion 608 possesses a limited circumferential extent, meaning that each of the protrusions is not an annular member possessing a 360° circumferential extent. The circumferential extent of the protrusion member 608 is preferably less than 180°. A range for the circumferential extent of the protrusions may be based on the circumferential distance between side branches of the vein.

The dissecting device 600 further includes or possesses a cutting and heating member 612. This cutting and heating member 612 is generally annular-shaped as seen in transverse cross-section, though does not possess 360° circumferential extent. That is, as described below and shown in FIG. 18B, the cutting and heating member 612 is C-shaped in transverse cross-section, meaning there is a break in the cutting and heating member 612 along the circumferential extent of the heating member 612. This break can accommodate the guide wire. The cutting and heating member 612 is separate from and movable relative to the dissecting member 602, is positionable at the distal end portion of the dissecting member 602 and is located inside the dissecting member 602. The cutting and heating member 612 is positionable at the base (proximal end) of the saw tooth-shaped distal end of the dissecting member 602. That is, the cutting and heating member 612 is positioned at the proximal end of the notches and protrusions 608 forming the saw tooth-shaped distal end 610 of the dissecting member. As the dissecting device 600 is moved along the vein (saphenous vein) during use of the dissecting device, side branches of the vein, such as the side branches 1100 illustrated in FIGS. 4A, 4B, 5A, 5C are received in the notches forming the saw tooth-shaped distal end 610 of the dissecting member 602 and are then cut by the cutting and heated heating member 612. In this regard, the cutting and heating member 612 is connected to an electrical lead 614 as illustrated in FIG. 18B so that the cutting and heating member 612 may be connected to a power source for heating the cutting and heating member.

Figure 20:
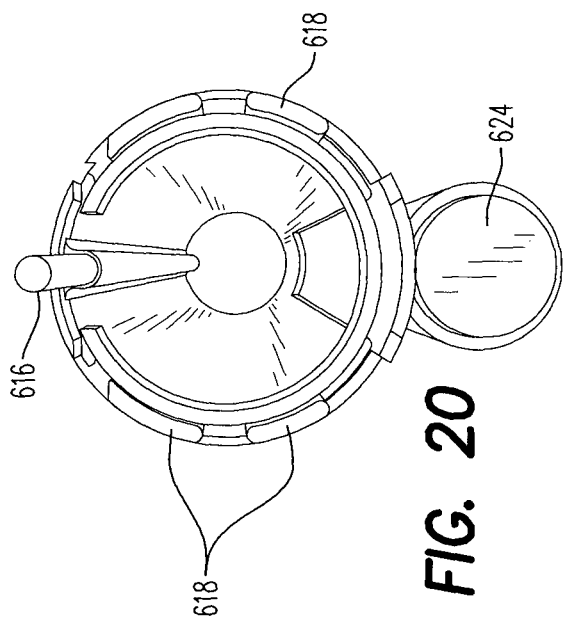
FIG. 20 is a front view of the dissecting member forming a part of the dissecting device shown in FIG. 18.
Figure 19:
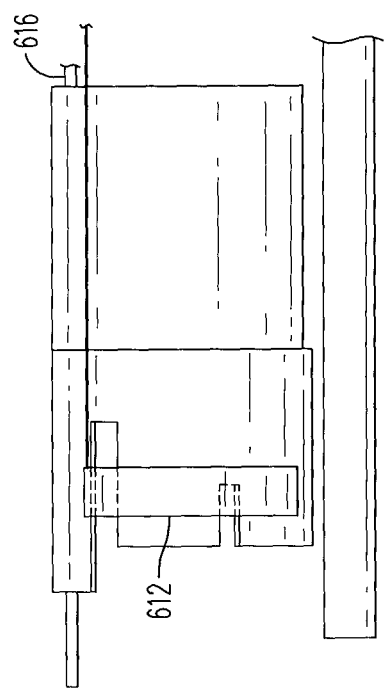
FIG. 19 is a side view of the dissecting member forming a part of the dissecting device shown in FIG. 18.

The dissecting member 602 is preferably a hollow elongated member (e.g., tubular member) with a lumen extending along its length. The dissecting device 600 is preferably used together with a guide wire 616 as illustrated in FIGS. 18-20. During use, the guide wire 616 is positioned in the lumen in the dissecting member 602.

A tubular member 620 is rotatably mounted on the outer surface of the dissecting member 602 at two spaced apart locations 622, 622 as generally illustrated in FIG. 18A. That is, the tubular member 620 can be rotated relative to the dissecting member 602. This tubular member 620 also includes or possesses an elongated receiving part 624 provided with a lumen configured to receive a viewing device or imaging device such as an endoscope, camera or the like. The tubular member 620 may have at least part of the lumen. For example, the tubular member has C-shape. With the viewing device 1002 positioned in the lumen of the tubular member or elongated receiving part 624, the user is able to view a viewing area or imaging area in front of the dissecting member 602 as the dissecting member 602 is moved through the living body along the vein.

The cutting and heating member 612 is an elongated member or possesses an elongated shape. The cutting and heating member 612 is located in the distal end portion of the dissecting member 618. In the illustrated embodiment, the cutting and heating member 612 and the dissecting member 602 are coaxial. The cutting and heating member 612 is located under the dissecting member 618 in a radial direction of the dissecting devise 600. That is, as described above, the cutting and heating member is positioned in the lumen in the dissecting member 602. The cutting and heating member 612 can be O-shaped, C-shaped or the like, and is positioned axially behind or at the base of the grooves or notches between the protrusions 608.

A method of using the dissecting device 600 to dissect a blood vessel (e.g., a vein such as a saphenous vein) may be generally similar to the method described above in that the method may include using the dissecting device 600 to dissect the blood vessel (including tissue (fat) covering the blood vessel), ligating and cutting the blood vessel, and then removing the severed or dissected blood vessel with the surrounding tissue from the living body. The method here involves several different aspects as discussed below.

Figure 21:
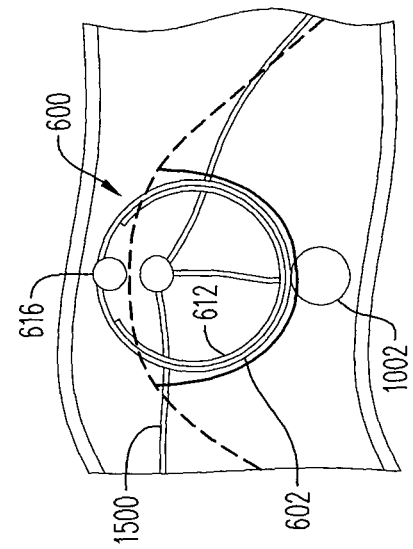
FIG. 21 is a front view of the dissecting member forming a part of the dissecting device shown in FIG. 18 illustrating the way in which the dissecting member interacts with the vein being dissected.

In the case of dissecting a vein (saphenous vein), for example, after identifying the location of the vein to de dissected, an incision is made in the living body (e.g., the leg of a patient) to provide an access site to the vein as well as the saphenous fascia surrounding the vein. The user then introduces the guide wire 616 into the living body by way of the incision, and moves the guide wire 616 along the vein 1000 in a known manner so it generally follows the vein 1000. The user may then hold the proximal portion of the dissecting device 600 and position the dissecting member 602 over the guide wire 616 so that the guide wire 616 is located in the lumen in the dissecting member 602. The dissecting member 602 is then advanced in the forward direction over the guide wire 616 to introduce the dissecting member 602 into the living body by way of the incision. The dissecting member 602 (with the cutting and heating member 612 positioned inside the dissecting member 602) is advanced to position the vein 1000 to be dissected into the lumen in the dissecting member 602. The dissecting member 602 and the cutting and heating member 612 are thus positioned in surrounding relation to the vein as illustrated in FIG. 21. The dissecting member 602 is then moved along the guide wire 616 so that the dissecting member 602 moves along the vein 1000. As the dissecting device 600 is moved along the guide wire 616, the presence of the protrusion member 608 can help stabilize the guide wire 1002 because the guide wire 616 is preferably positioned immediately adjacent the protrusion member 608. As the dissecting device 600 is moved along the guide wire, the cutting and heating member 612 operates to perform dissection. As the dissecting device 600 is moved along the guide wire 616, the side branches of the vein are positioned in the grooves or notches between the protrusions 608, and are cut and heated by the cutting and heating member 612 after the side branches of the vein are guided between the distal end portions (grooves) of the dissecting member 618. The disclosed method thus involves cutting a side branch of the vein while at the same time stopping bleeding using the cutting and heating member 612.

FIG. 20 illustrates that the elongated receiving part 624 of the tubular member 620 possesses a 360° circumferential extent. But it is also possible that the elongated receiving part 624 can exhibit a circumferential extent less than 360°, for example by possessing a C-shaped cross section. The tubular member 620 can thus be configured differently than illustrated, though should preferably be configured to be rotatably mounted on the dissecting member 602 and to receive and hold/guide a viewing device or imaging device 1002.

The method associated with the use of the dissecting device 600 shown in FIGS. 18-21 involves inserting the dissecting member 602 between a first tissue and a second tissue. That is, the protrusion member 608 can dissect the first tissue and the second tissue from one another. The dissecting device disclosed here is configured so that as the dissecting device is being advanced, the dissecting member 602 dissects the tissue/vein while the cutting and heating member 612 cuts side branches of the vein. This occurs at the same time because the dissecting member 602 and the cutting and heating member 612 are positioned relatively close to one another. In this embodiment, the cutting and heating member 612 is axially movable. The cutting and heating member 612 is axially movable relative to the dissecting member 602.

FIGS. 22-26 illustrate another embodiment of the dissecting device 600'. Many of the features of this embodiment of the dissecting device 600' are similar to the embodiment of the dissecting device 600 illustrated in FIGS. 18-21, and common features between the two embodiments are identified by common reference numerals. A detailed discussion of the features associated with the dissecting device 600' which have already been described above will not be repeated.

This embodiment of the dissecting device 600' shown in FIGS. 22-26 differs from the earlier embodiment of the dissecting device 600 in that the embodiment shown in FIGS. 22-26 includes or possesses a covering member 628 positioned in overlying or covering relation to the lumen in the tubular member 620 that receives the viewing device 626. The covering member 628 possesses a cap or cover 630 connected to a mounting portion 632 that is rotatably mounted on the portion of the tubular member 620 housing the viewing device 626. The covering member 628 also includes or possesses an elongated tubular (hollow) member 634 that projects rearwardly (in the proximal direction) from the mount 632. The covering member 628 also possesses a lumen 636 that passes through the mount 632 and communicates with the hollow interior of the elongated tubular member 634. The lumen 636 possesses an open distal end that faces in the direction of the cap or cover 630. The lumen in the covering member 628 is connected to a source of fluid 638 schematically illustrated in FIG. 22B. The fluid from the fluid source 638 passes through the lumen 636 and is ejected from the open distal end of the lumen to clear the field of view for the viewing device 626. The fluid source can be any desired source of fluid, an example of which is carbon dioxide ($CO_2$).

The covering member 628 is preferably configured so that the covering member overlies or covers an area immediately in front of the viewing device 626. The cap 630 prevents tissue from blocking the field of view of the viewing device 626, thus allowing the dissecting member to be properly positioned to cut or sever a side branch(es) 1200 of the vein. In addition, fluid can be introduced by way of the lumen 636 to clear away the field of view for the viewing device 626. The covering member 628 (the cap 630 and the fluid lumen) thus advantageously helps prevent tissue from blocking the viewing device (e.g. endoscope, camera, etc.). The cap 630 is also configured and positioned so that an imaginary continuation of the viewing device 626 in the forward direction intersects at least a part of the cap of 630.

FIG. 26 illustrates one way of using the dissecting device shown in FIGS. 22-26. As illustrated, the side branch 1200 of the vein 1000 is positionable between the cover or cap 630 and the viewing device 626.

This embodiment of the dissecting member 600' also possesses the grooves 618 constituting distal portions for receiving side branches. This embodiment shown in FIGS. 22-26 is configured so that the cutting member 612, which is coaxial with the dissecting member 602, is positioned on the outer surface of the dissecting ember 602 (i.e., exterior of the dissecting member 602). But it is also possible for the cutting member 612 to be coaxial with the dissecting member 602 and positioned inside the dissecting member 602.

Figure 22A:
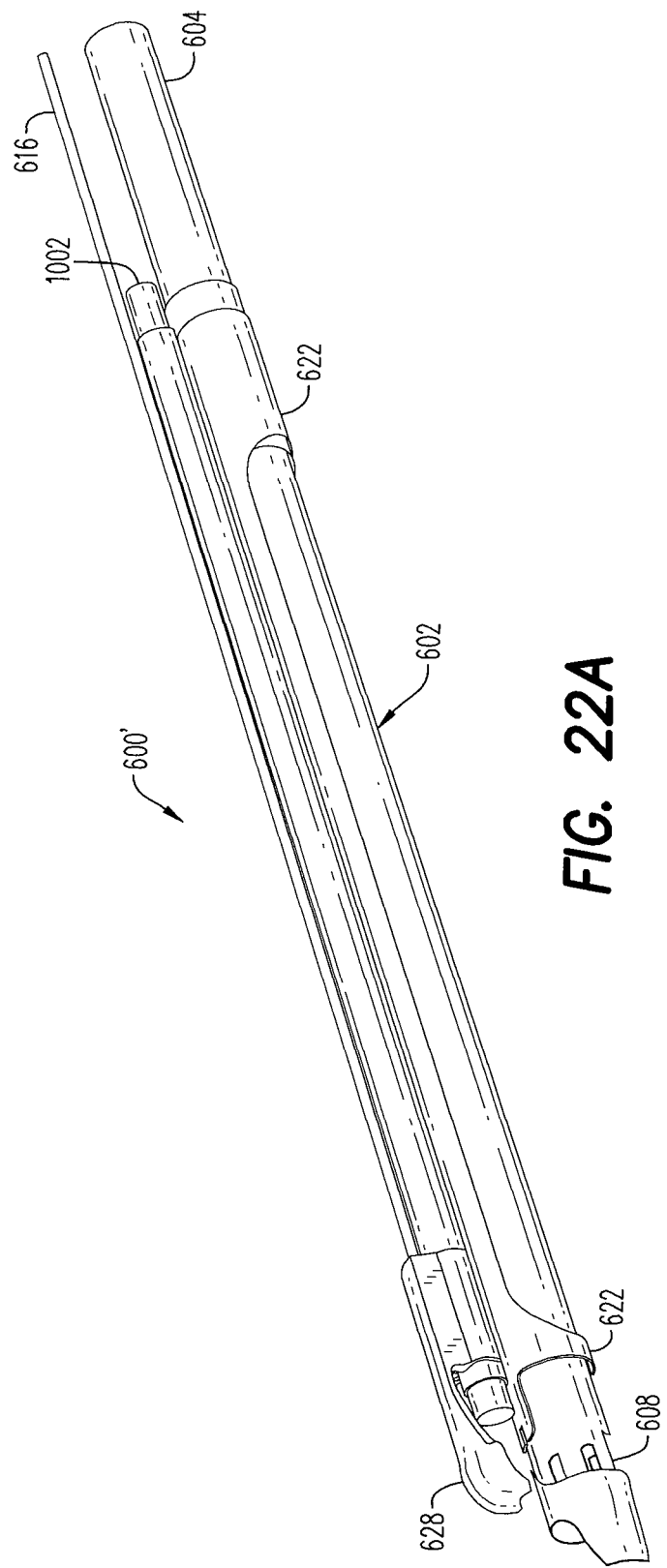
FIGS. 22a and 22B are perspective and exploded views respectively of another embodiment of the dissecting device.
Figure 22B:
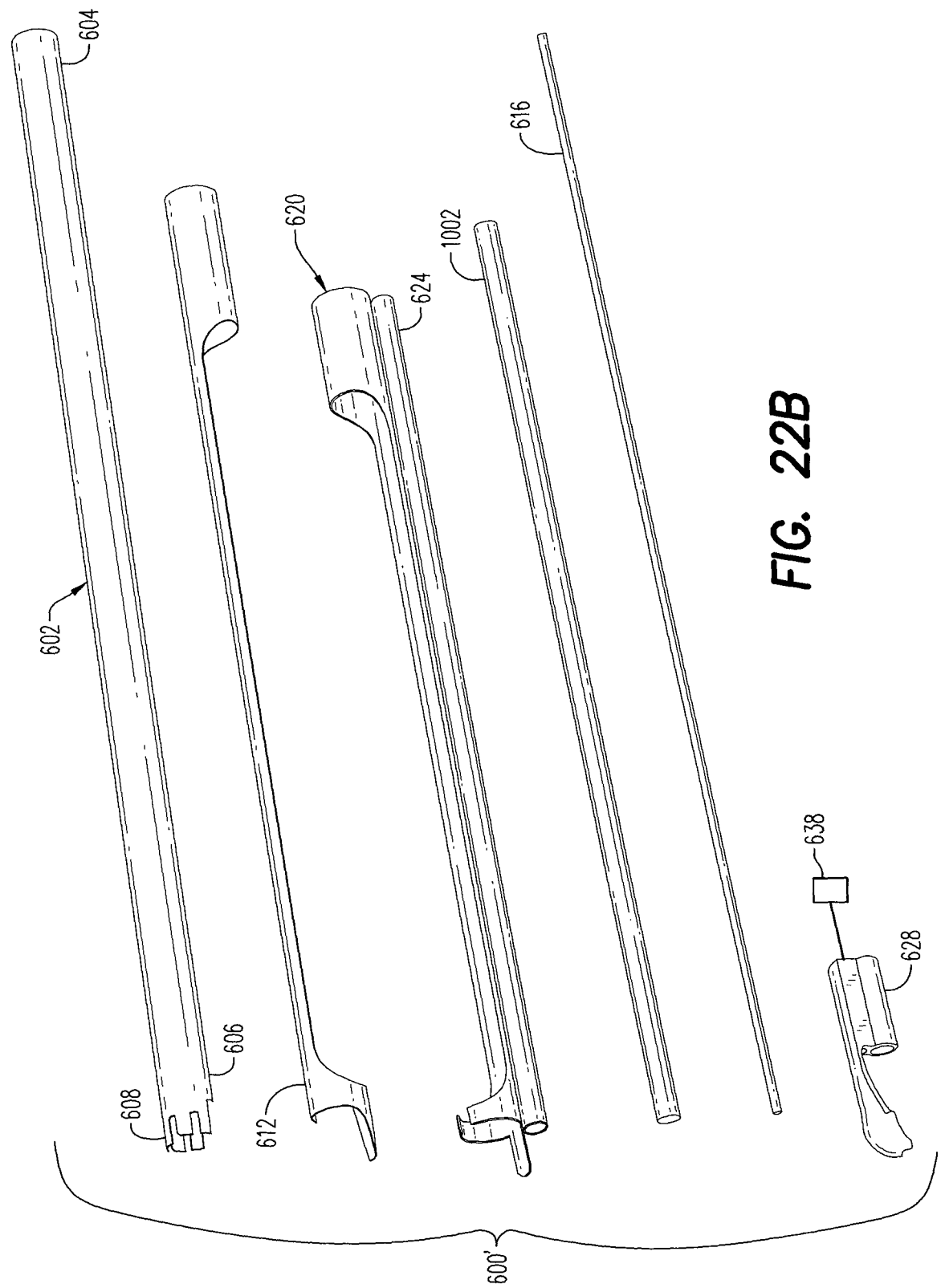

FIGS. 22A and 22B illustrate that this embodiment of the dissecting device 600' need not include a cutting and heating element. Instead, the dissecting device 600' includes or possesses a cutting element 612. But the dissecting device 600' can be provided with the heating member 612 if desired as shown schematically in FIG. 25. If the dissecting device 600' is configured without the heating member, the manner of operation of the dissecting device is generally as follows. After confirming the location of the vein to be dissected, an incision is made in the patient (i.e., the living body) to gain access to the vein. The dissecting device 600' is then introduced into the living body and moved along the vein 1000. This embodiment of the dissecting device 600' does not necessarily require a guide wire as in the earlier embodiment. In the earlier embodiment of the dissecting device 600, the viewing device 1002 is spaced relatively far from the vein 1000 and so the guide wire is useful in helping to guide the movement of the dissecting device 600 along the vein. The embodiment of the dissecting device 600' shown in FIGS. 22-26 is configured so that during use, the viewing device 626 is positioned relatively close to the vein 1000. A guide wire is thus preferably not used or necessary. As the dissecting device 600' is moved along the vein, the cutting device cuts fat surrounding the vein. The viewing device used during this forward movement of the dissecting device can help guide the movement of the dissecting device even though the cap/cover 630 of the covering member 628 may hinder the field of view. When the dissecting device 600' approaches a side branch 1200 of the vein 1000, the covering member 628 is rotated into a position like that illustrated in FIG. 26 so that the side branch 1200 may be cut using the cutting device 612. Thus, the viewing device 626 permits confirmation of the cutting of the side branch 1200. The vein can thus be severed after one forward axial movement of the dissecting device 600'.

In the embodiments of the dissecting device 600, 600' shown in FIGS. 18-26, the size of the lumen that houses the viewing device 626 (i.e., the cross-sectional area transverse to the axis of the lumen) is larger than the size of the lumen 630 along which fluid is directed to clear the field of view of the viewing device.

Both embodiments of the dissecting device 600, 600' shown in FIGS. 18-26 can also utilize a dissecting member in the form of bi-polar electrodes.

Figure 27A:
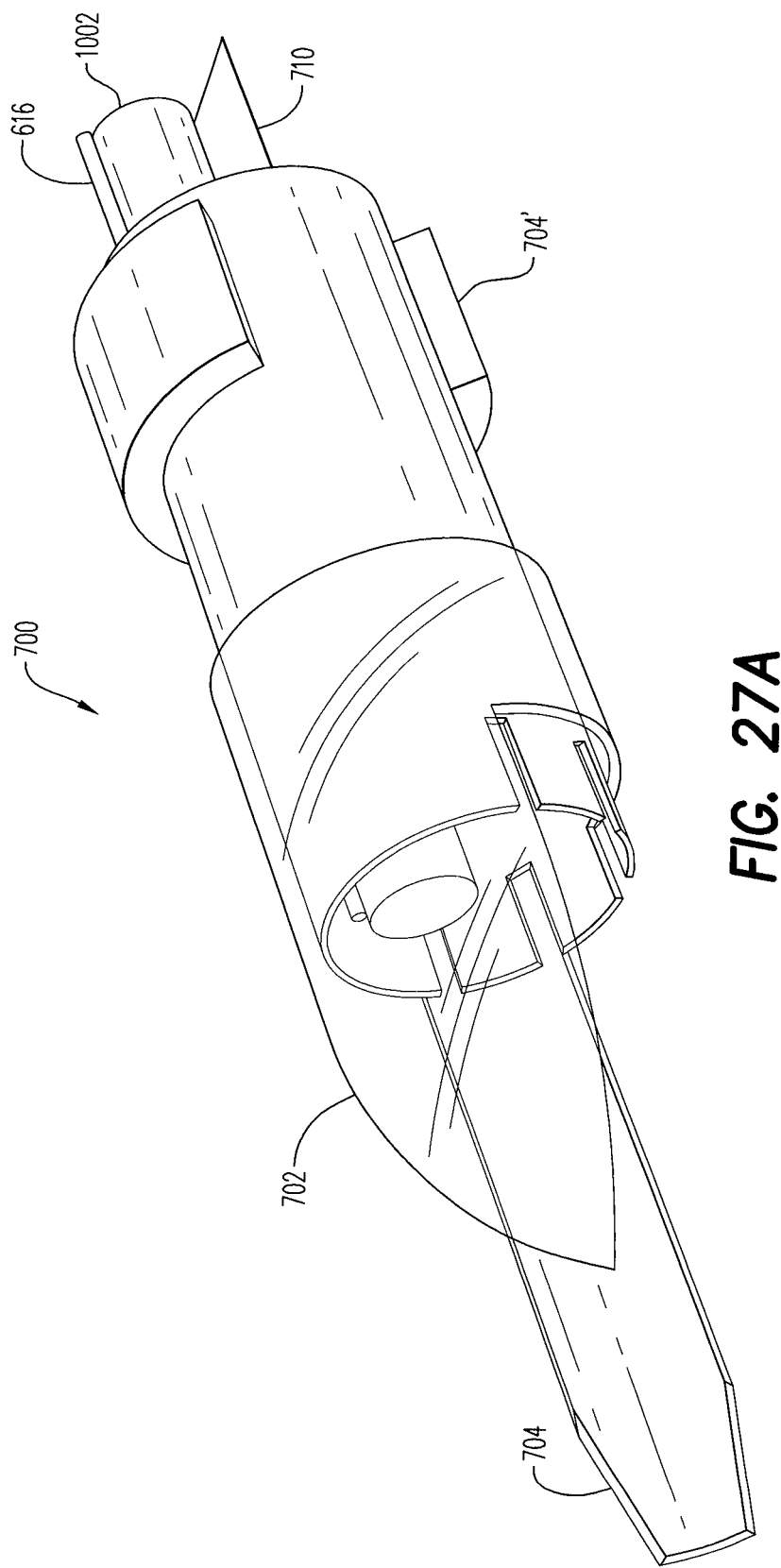
FIGS. 27A and 27B are perspective and exploded views of another embodiment of the dissecting device.
Figure 27B:
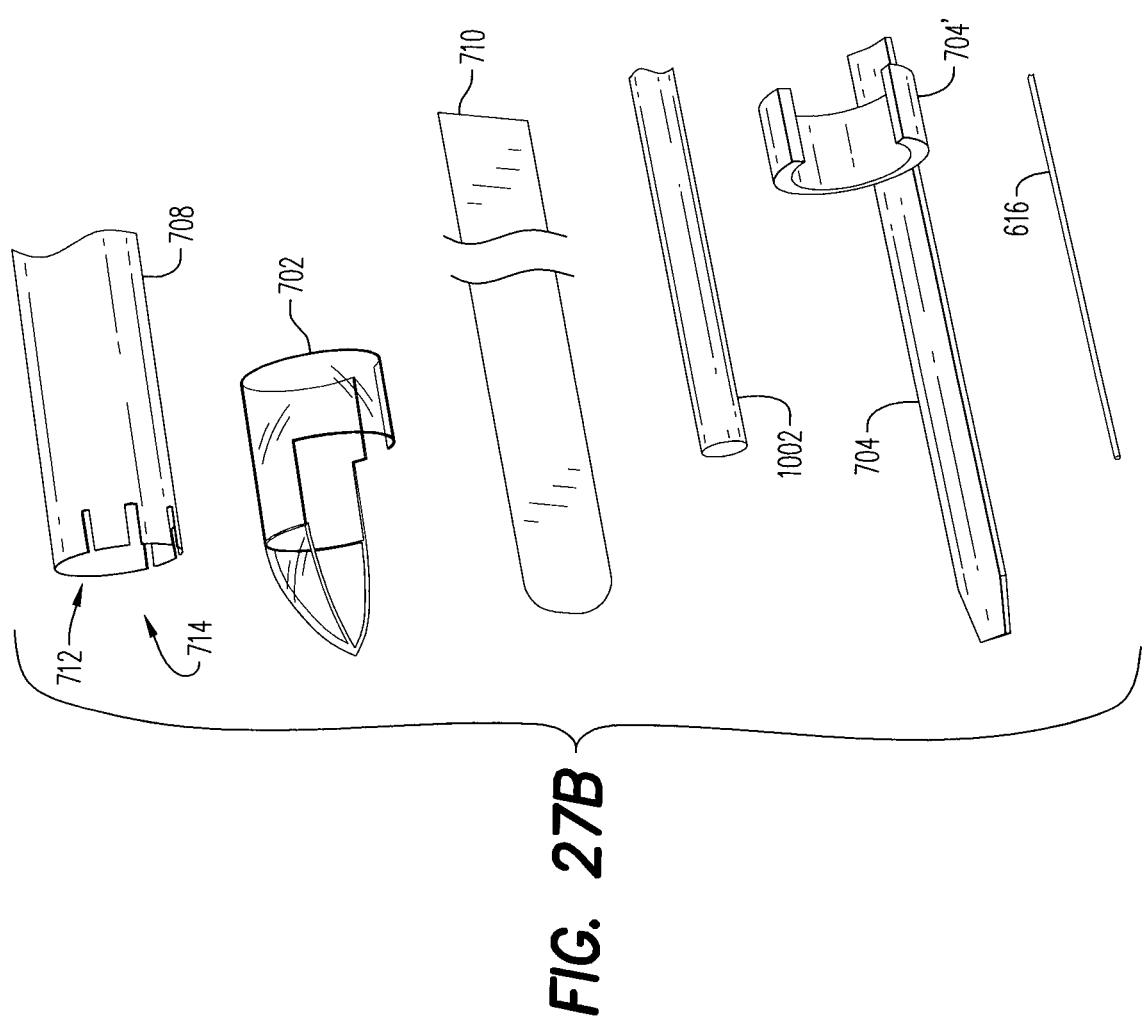
Figure 28:
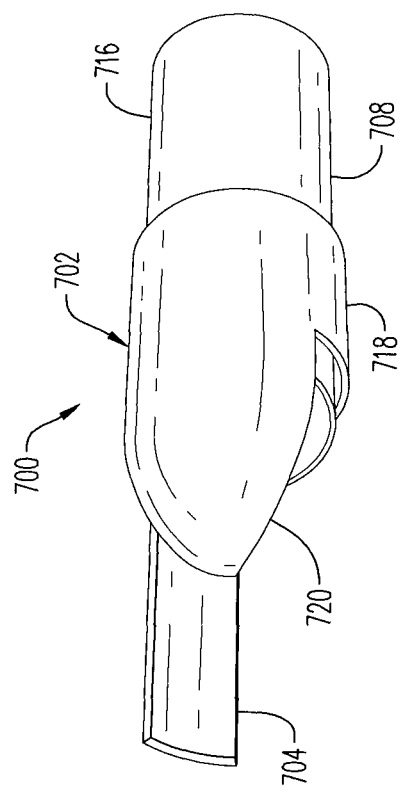
FIG. 28 is a perspective view of the dissecting device shown in FIG. 27.
Figure 29:
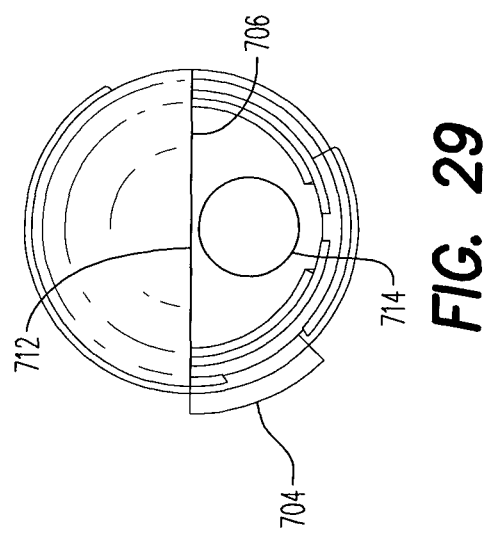
FIG. 29 is a transverse cross-sectional view of the dissecting device shown in FIG. 27.

FIGS. 27-29 illustrate a further embodiment of a dissecting device. This embodiment of the dissecting device 700 includes or possesses a capping member 702, a cutting member 704, and a tubular member 708. The tubular member 708 is elongated and hollow along its entire axial extent. FIGS. 27A, 27B and 29 illustrate that at least the distal portion of the tubular member 708 is provided with a cover 710 that divides the interior of the tubular member 708 (lumen in the tubular member 708) into an upper portion (half) in which is located a first lumen 712, and a lower portion (half) in which is located a second lumen 714. The first lumen 712 is configured to receive a viewing device or an imaging device (e.g., an endoscope, camera or the like) while the second lumen 714 is configured to receive an ablation device (heating device).

The cover member 710 that divides the interior of the tubular member 708 into two parts maybe a clear cover member. This can help facilitate viewing a position of the vein with a viewing device and facilitate moving the viewing device along the vein.

The capping member 702 is mounted on and fixed to the distal end portion 716 of the tubular member 708. In the illustrated embodiment, the capping member is mounted on the outer periphery of the tubular member 708 so that the proximal portion of the capping member 702 encircles the outer periphery of the tubular member 708. As illustrated in FIGS. 27 and 28, the capping member 702 possesses a hollow cylindrical or annular proximal portion 718 and a curvilinearly tapering distal portion 720. The proximal portion 718 encircles and is fixed to the distal end portion 716 of the tubular member 708. The distal portion 720 of the capping member 702 is shaped as one-half of a curvilinearly tapering cone.

The cutting member 704 is mounted on the tubular member 708. In the illustrated embodiment, the cutting member 704 possesses a generally C-shaped proximal portion 704' that is mounted on and encircles the outer periphery of the tubular member 708 at a position proximal of the capping member 702. The cutting member 704 is movable relative to the tubular member 708 and the capping member 702. That is, the cutting member 704 is movable (slidable)

along a half-circle movement path from the position on the left side of the bottom half shown in FIG. 29 to the corresponding position on the right side of the bottom half in FIG. 29.

As in the earlier embodiment described above and shown in FIGS. 22-26, the capping member 702 covers and protects the viewing device positioned in the first lumen 712 to prevent tissue from blocking the viewing device. The tapered shape of the capping member 702 allows the dissecting device 700 to be moved through the living body along the vein relatively easily. When the dissecting device 700 being moved along the vein encounters a side branch of the vein (e.g., the side branch 1100 shown in FIGS. 4A, 4B, 5A, 5B), the dissecting device 700 may be manipulated or rotated to position the side branch inside the capping member 700 between the viewing device located in the first lumen 712 and the distal-most end of the capping member 702. The viewing device positioned in the first lumen 712 can thus be used to view the side branch and facilitate the cutting of the side branch by the sliding movement of the cutting movement 704.

The cutting member 704 is generally used to cut the side branches of the vein, though may be used throughout the dissecting procedure.

The capping member 702 possesses a window 706. This window simply results from the configuration of the distal portion 720 of the capping member 702, namely that the capping member is open along half of its circumference. The cutting member 704 is located between the tubular member and the capping member 702 in the radial direction of the dissecting device 700.

Referring to FIG. 29, the window spanning across the capping member 702 possesses one edge at the left and another edge at the right. The width-wise extent of the window thus extends from the one edge (left edge) to the opposite edge (right edge). The cutting member 704 is turnable or slidable (rotatable) from one edge of the window to the opposite edge of the window. The window may be transparent member.

The cutting member 704 may be provided with a lumen. Such a lumen may be configured to receive or house an electrode and/or an ablation device which serves as a heating device to help stop bleeding. The cutting member is also configured to move in the axial direction, and the distal-most end of the cutting member 704 is positioned distally of (forward of) the distal-most end of the capping member 702 such as illustrated in FIGS. 27 and 28. The distal-most end of the cutting member 704 may also be positioned distally of (forward of) the distal-most end of the dissecting member.

The window member may have a longitudinal opening and may be transparent. A window member may be included that covers the window 706. The longitudinal opening may be at least a part of the longitudinal length of the window member. The longitudinal a distal portion of the capping member to this side of a proximal end of the inner surface of the capping member. A space can be between the window member and an inner surface of the capping member.

Figure 30:
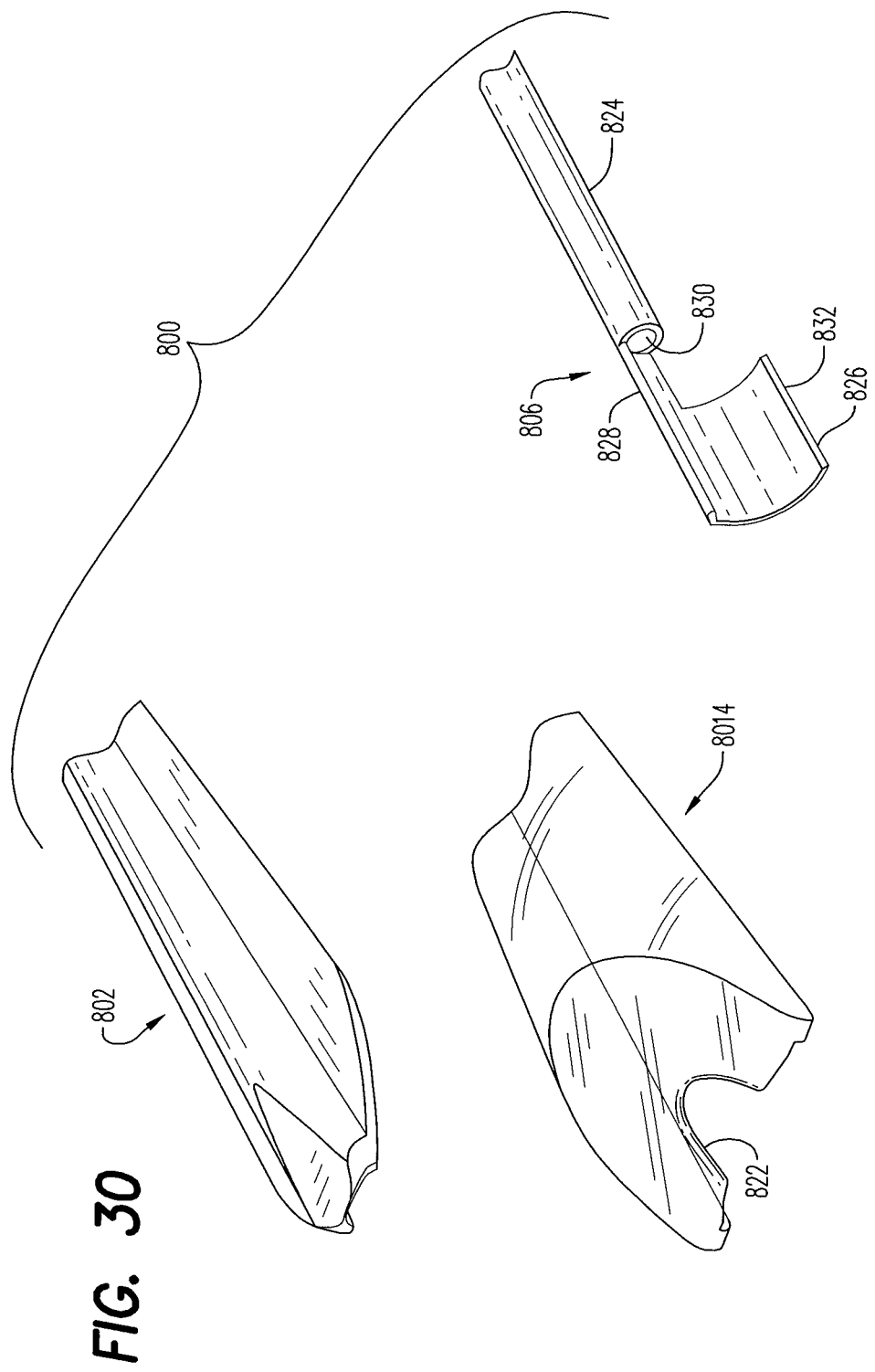
FIG. 30 is a top perspective view of another embodiment of the dissecting device.

FIG. 30 illustrates a further embodiment of a vein harvesting device or vein dissecting device. This embodiment of the vein dissecting device 800 includes or possesses an assembly of three parts or members, namely a dissecting member 802, a covering member 804 and a cutting member 806. As will be described below in more detail, during use of the vein dissecting device 800, the dissecting member 802 is first positioned under the covering member 804 and then is later removed from the covering member 804. The cutting member 806 is then positioned under the covering member 804.

FIG. 30 illustrates just the distal portion of the dissecting member, it being understood that the dissecting member 802 is an elongated member as is apparent from, for example, the illustration in FIG. 33C. The dissecting member 802 is shown in more detail in FIGS. 31A and 31B. The dissecting device 802 is an elongated member which, in the illustrated embodiment, possesses a rounded and longitudinally extending central portion 808 and two longitudinally extending lateral wings 810 on opposite sides of the central portion 808. The dissecting member 802 also possesses a generally flat bottom surface 812 provided with a longitudinally extending and centrally located opening 814 that communicates with and opens into a lumen 816 configured to receive a viewing device or imaging device 1002 (e.g., an endoscope, camera or the like). The opening 814 is centrally located with respect to the width-wise extent of the dissecting member 802. The top surface 817 of the distal end portion of the dissecting member 802 is flattened as shown in FIGS. 30 and 31A to allow the dissecting member 802 to be accommodated in the covering member 804 as shown in FIGS. 33A-33C, and so that when the dissecting member 802 and the covering member 804 are assembled as shown in FIGS. 33A-33C, a relatively smooth transition exists between the distal end portion of the dissecting member 802 and the distal end portion of the covering member 804.

Figure 31A:
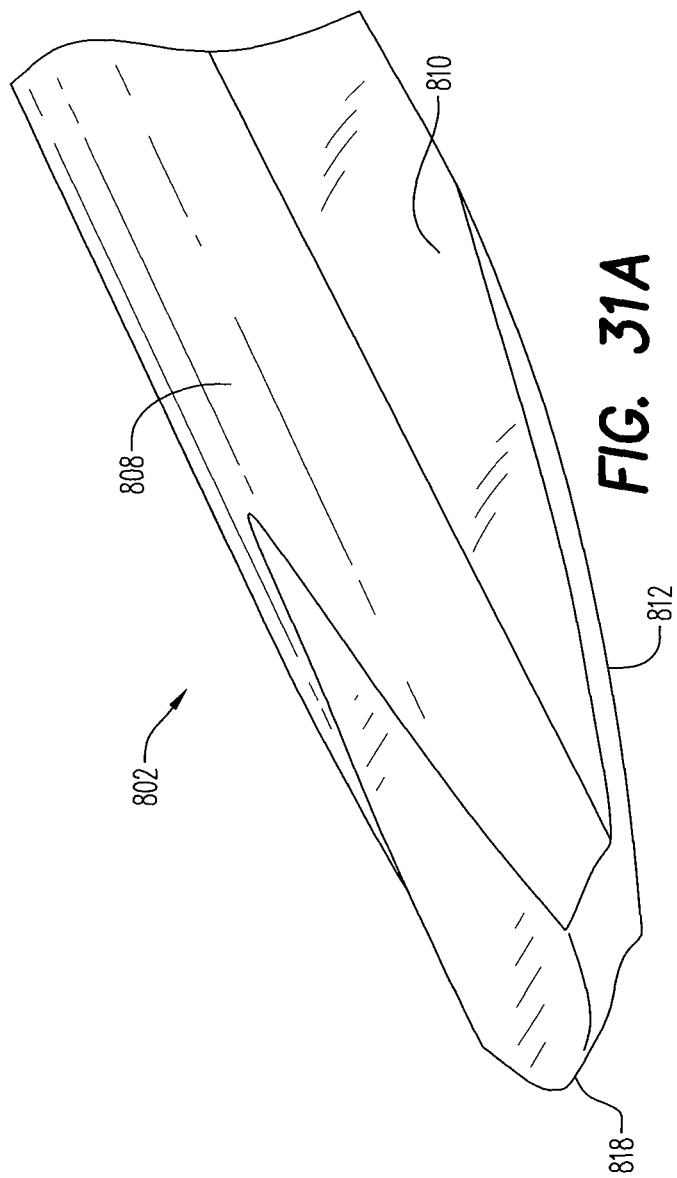
FIG. 31A is a perspective view of a part of the dissecting member forming a part of the dissecting device illustrated in FIG. 30.
Figure 31B:
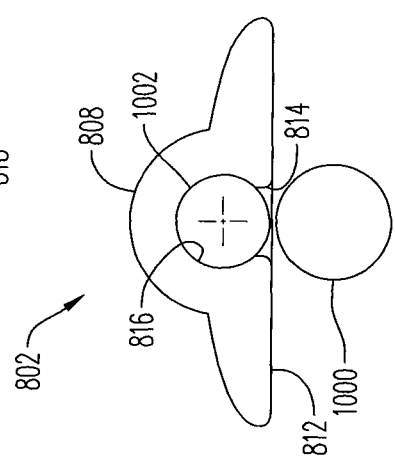
FIG. 31B is a cross-sectional view of the dissecting member forming a part of the dissecting device illustrated in FIG. 30.

FIG. 31B illustrates the dissecting member 802 in transverse cross-section and shows the viewing device 1002 positioned in the lumen 816 of the dissecting member 802. The viewing device 1002 allows the area in front of the dissecting member 802 to be viewed while the dissecting member 802 is being advanced or moved in the forward direction through the living body and along the vein.

The distal-most end 818 of the dissecting member 802 is rounded as seen in FIGS. 30 and 31A to help facilitate relatively smooth movement of the dissecting member 802 through the living body and to help facilitate dissection of the vein from surrounding tissue.

Figure 32A:
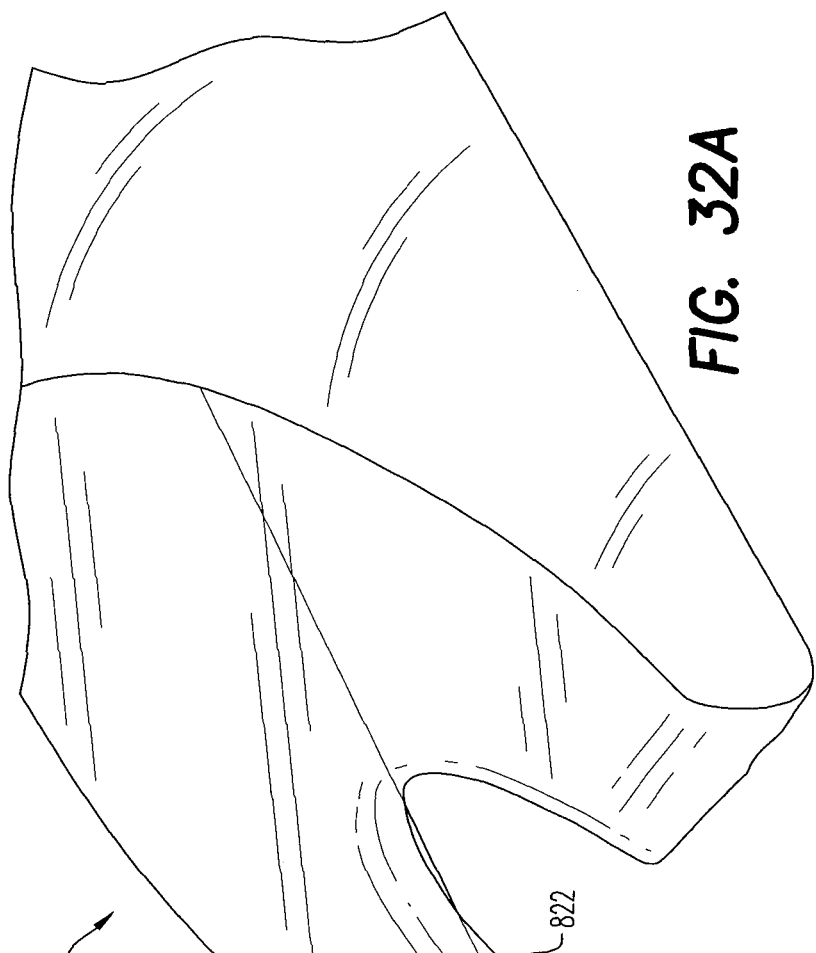
FIG. 32A is a perspective view of a part of the covering member forming a part of the dissecting device illustrated in FIG. 30.
Figure 32B:
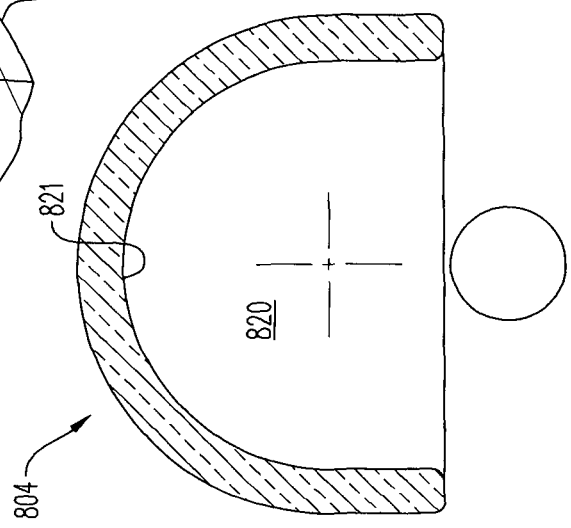
FIG. 32B is a cross-sectional view of the covering member forming a part of the dissecting device illustrated in FIG. 30.

FIG. 30 illustrates just the distal portion of the covering member 804, it being understood that the covering member 804 is an elongated member as is apparent from, for example, the illustration in FIG. 33C. The covering member 804 is shown in more detail in FIGS. 32A and 32B. The covering member 804 possesses an elongated shape along its longitudinal extent and exhibits a dome-shaped configuration (somewhat hemispherical shape) in transverse cross-section as illustrated in FIG. 32B. A hollow space or lumen 820 is positioned at the underside of the covering member 804. This hollow space or lumen 820 is specifically configured to receive the dissecting member 802 as illustrated in FIGS. 32A and 32B. That is, after the dissecting member 802 is inserted into the living body, the covering member is inserted into the living body and advanced to a position covering or on top of the dissecting member 802 to form the assembly shown in FIGS. 33A-33C. The covering member 804 may be positioned in covering relation to the dissecting member 802 before the dissecting member 802 is positioned in living body, or after the dissecting member 802 is positioned in living body but before moving the dissecting member 802 along the vein. As described in more detail below, the hollow space or lumen 820 in the undersurface of the covering member is also configured to receive the cutting member 806 after the dissecting member 802 is removed from the covering member 804.

As illustrated in FIG. 32A, the distal portion of the covering member 804 possesses a U-shaped recess 822 that opens into and communicates with the hollow space or lumen 820. This U-shaped recess also opens to the distal end of the covering member 804 so that the dissecting member 802 can protrude at the distal end of the covering member as shown in FIGS. 33A and 33C. That is, when the covering member 804 is positioned over or in covering relation to the dissecting member 802, the distal end portion of the dissecting member 802 protrudes through the U-shaped recess and protrudes distally beyond the distal-most end 805 of the covering member 804 as illustrated in FIGS. 33A and 33C.

The cutting member 806 includes or possesses an elongated member 824 and a blade 826 that are connected to one another by a connecting member 828. As illustrated in FIG. 30, the elongated member 824 is a hollow member that possesses a lumen 830 extending along the entire length of the elongated member 824. The lumen 830 is configured to receive a viewing device or imaging device (e.g., an endoscope, camera, etc.). This viewing device helps facilitate the use and operation of the cutting member 806 during operation of the dissecting device 800 allowing the user to view the area in front of the cutting member 806.

The blade 832 is a curved blade possessing a curved (convex) outer surface 832 and an oppositely facing curved (concave) inner surface. The curvature of the outer surface 832 of the blade 826 is selected to closely match the curvature on the inner surface 821 of the covering member. Thus, when the elongated member 824 of the cutting member 806 is rotated to rotate or turn the curved blade 826 of the cutting member 806 while the blade 826 is positioned underneath the cover member 804 (i.e., when the cutting member 806 is positioned in the underside of the covering member 804 as shown in FIG. 34), the outer surface 832 of the blade 826 closely corresponds to and follows the curved inner surface (under surface) 821 of the cover member 804 as can be appreciated from FIGS. 34 and 35. FIG. 35 illustrates the cutting member 806 positioned in the cover member 804 with the viewing device 1002 positioned in the lumen inside the elongated member 824. FIG. 35 also shows that the proximal end of the elongated member 824 can be connected to a handle 834 or other suitable operating device to rotate or turn the blade 826 of the cutting member 806.

FIG. 33C illustrates an example of the elongated nature of the covering member 804 positioned over the elongated dissecting member 802. FIG. 33C illustrates that the proximal end portion of the covering member 804 can be provided with a series of axially spaced apart ridges 807. These ridges 807 can help facilitate holding by the user.

As described above, during use of the dissecting device 800, the dissecting member 802 by itself is first positioned in the living body by way of an incision formed in the living body. The dissecting member 802 is then moved along the vein for a distance. The covering member 804 is then introduced into the living body and positioned in covering relation to the dissecting member 802 as shown in FIGS. 33A-33C. During use, the covering member may be pressed so that the covering member doesn't move. The cutting member rotates along an inner surface of the covering member toward out of an inner cutting member to cut the vein and tissue that is surrounding the vein from the tissue.

After the dissecting member 802 is removed from the covering member 804, the cutting member 806 is introduced into the lumen 820 (the underside) of the covering member 804. FIG. 35 illustrates, in cross-section, the cutting member 806 positioned in the lumen in the underside of the covering member 804. The cutting member 806 is preferably positioned in the lumen 820 of the covering member 804 in a manner such as illustrated in FIG. 35 in which the cutting member 806 is positioned close to or in contact with one of the interior sides of the covering member 804. With the cutting member 806 positioned in such a manner, the cutting member 806 may be rotated or turned to effect desired cutting.

As the cutting member 806 is introduced into the lumen 820 in the underside of the covering member 804, the viewing device 1002 may be positioned in the lumen 830 in the elongated hollow member 824 of the cutting member 806. This allows the cutting member 806 to be more easily operated or manipulated to the correct position. It is also possible to introduce the viewing device 1002 into the lumen 830 in the elongated hollow member 824 of the cutting member after the cutting member 806 is positioned in the lumen 820 in the underside of the covering member 804. The viewing device 1002 can be used during the cutting operation to view in front of the cutting blade 826.

After the cutting member 806 is introduced into the lumen 820 in the underside of the covering member 804, it is possible to rotate the elongated member 824, or the handle 834 connected to the elongated member 824, to rotate or turn the blade 826. The blade 826 thus rotates about an axis represented by the central axis 825 of the elongated member 824. This rotation axis 825 is offset from the center of curvature of the concavely curved blade 826. Rotating or turning the blade 826 causes the blade 826 to move from the position shown in FIG. 36 to the position in which tip end of the blade 826 reaches the opposite side edge 809 of the covering member 804. After the cutting member is rotated to cut away the tissue from the vein, the cutting member may be rotated back to the FIG. 36 position and then the cutting member may be moved forward and once again rotated. This process or operation may be repeated.

After the desired length of the vein has been separated from the surrounding tissue, the covering member 804 and the cutting member 806 are removed from the living body, the ends of the dissected vein are ligated and then cut (severed), and the severed vein is removed from the living body for use in the desired manner.

FIG. 37 illustrates a slightly modified version of the dissecting device depicted in FIGS. 30-36. This embodiment of the dissecting device 900 shown in FIG. 37 includes or possesses an assembly comprised of a dissecting member 902, a covering member 904 and a cutting member 906. These three members 902, 904, 906 are generally similar to the dissecting member 802, the covering member 804 and the cutting member 806 respectively described above, except for the following differences.

The embodiment of the elongated dissecting member 902 shown in FIG. 37 is a bit more streamlined in configuration and possesses a more rounded or curved distal-most end to facilitate movement through the living body during dissection of the vein. The same is also true of the covering member 904 as it also possesses a more streamlined and rounded appearance, particularly a more rounded distal-most end.

The cutting member 906 shown in FIG. 37 differs from the embodiment of the cutting member shown in FIG. 30 in that the cutting member 906 possesses a cutting portion defined by a pair of axially spaced apart blades 926. The two blades 926 are axially spaced apart so that a space exists between the two blades as shown in FIG. 37. By virtue of the two-blade configuration of the cutting member 906 shown in FIG. 37, side branches of the vein can rather easily move between the two-blade configuration and be cut by the cut portion.

The use of the dissecting device or assembly 900 shown in FIG. 37 is similar to that described above which reference to the dissecting device or assembly illustrated in FIGS. 30-36.

Figure 38:
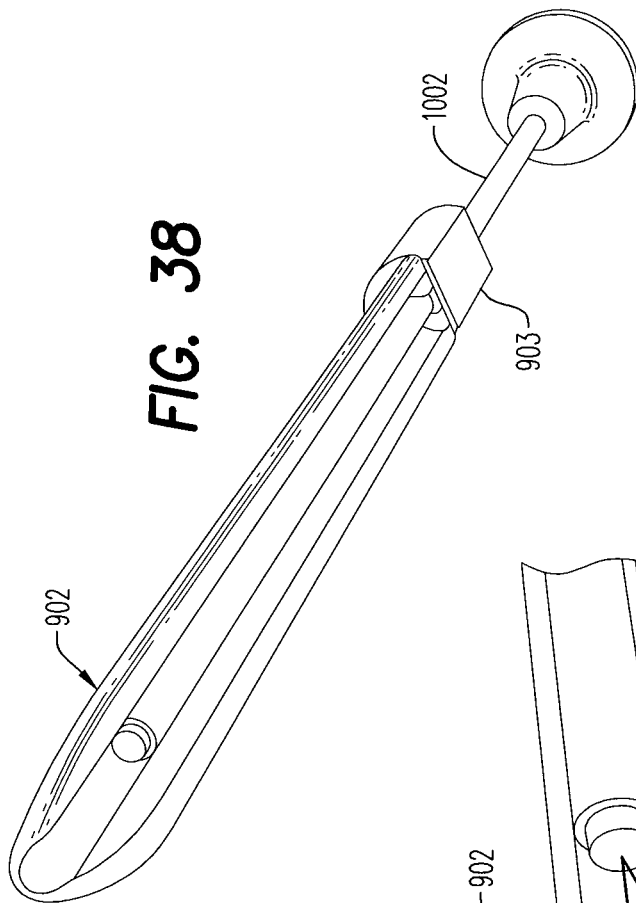
FIG. 38 is a bottom perspective view of the dissecting member forming a part of the dissecting device shown in FIG. 37 illustrating the viewing device positioned in the underside lumen.
Figure 39:
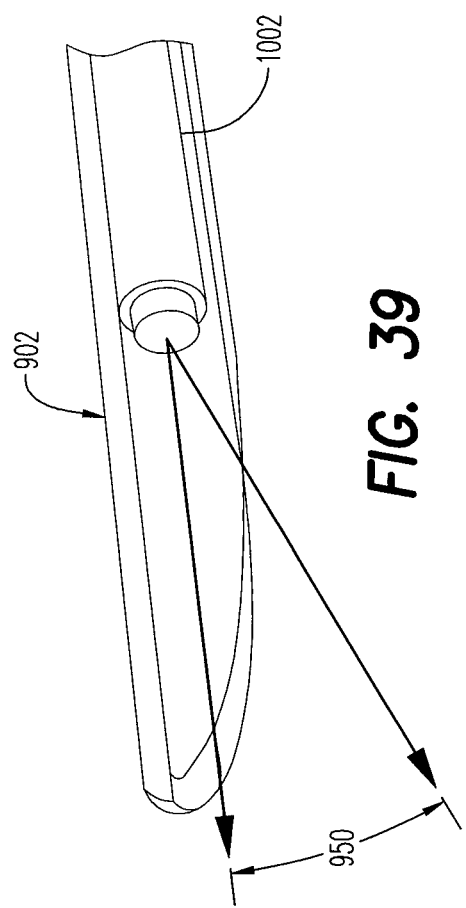
FIG. 39 is a bottom perspective view of the dissecting member forming a part of the dissecting device shown in FIG. 37 illustrating the field of view of the viewing device positioned in the underside lumen.

FIGS. 38 and 39 illustrate the dissecting device 902 as seen from below. FIGS. 38 and 39 both depict the viewing device or imagining device 1002 positioned in the lumen in the underside of the dissecting device 902. FIG. 38 shows that proximal end portion of the dissecting device 902 can be provided with a guide 903. This guide 903 possesses an axially extending through hole that receives the viewing device 626. The through hole in the guide 903 may be configured to relatively closely match the outer diameter of the viewing device 626 to help guide the viewing device 626 in the forward intended direction.

FIG. 39 generally illustrates the field of view 950 associated with the viewing device 1002. This field of view 950 allows the dissecting member 902 to be moved in the living body and along the vein (saphenous vein) while viewing the location of the vein to avoid contacting and possibly damaging the vein.

The covering member shown in FIGS. 30-33 is configured in a way that provides a relatively tight space at the distal end of the covering member. On the other hand, the configuration of the covering member shown in FIG. 36 provides a relatively larger space at the distal end. The configuration of the space can have an effect on the operability of the cutting member.

FIGS. 40-42 illustrate a slightly different embodiment of the covering member. As described above with reference to FIG. 38, the proximal portion of the dissecting member 802 includes or possesses an integrally formed viewing device holder serving as a guide for the viewing device 1002. In the embodiment shown in FIGS. 40-42, the holder for holding the viewing device is separate from and connectable to the covering member. As illustrated in FIG. 40, the proximal portion 1009 of the covering member 1004 is hollow and possesses a space 1007 for receiving the viewing device holder 1005. A ledge 1011 is located in the holder space 1007, on opposite sides of the holder space 1007, to receive the holder 1005. The flat bottom surface of the holder 1005 rests on the ledges 1011 on opposite sides of the space 1007, and the curved upper surface 1013 of the distal portion of the viewing device holder 1005 matches the curved inner surface overlying the holder space 1007. Thus, when the holder 1005 is slid into the holder space 1007 as illustrated in FIG. 41, the holder 1005 is supported and held in place by the ledges 1011 and the overlying curved surface defining the upper boundary of the holder space 1007. After the holder 1005 is positioned in the holder space 1007 of the covering member 1004, the viewing device 626 m may be introduced into the lumen 1015 in the holder. The viewing device 626 is thus held in place and properly guided.

FIGS. 43 and 44 illustrate additional details associated with the cutting member 906 forming a part of the dissecting device 900 depicted in FIG. 36. The cutting member is configured so that each of the blades 926 includes or possesses an electrode 952. The blades 926 also possess bipolar elements. The side branches of the vein are able to relatively easily come between or move between the two-blade configuration to be cut by the cut portion.

The dissecting devices 952, 926 may be bi-polar electrodes.

FIG. 45 illustrates an embodiment of the cutting member in which a double cutting portion is provided. That is, the connecting part of the cutting member is connected to the middle of the blade, and both sides or ends of the blade are provided with triangular-shaped projections (i.e., a sawtooth profile). The embodiments of the cutting member shown in FIGS. 30, 37 and 45 are able to cut when the cutting member is being rotated in only one direction, whereas the embodiment of the cutting member shown in FIG. 45 is able to cut when the cutting member is being rotated in either direction.

All embodiments of the device and method disclosed here can be used in operations other than a living body. That is, the device and method can be used with other bodies such as a cadaver and a simulator intended to simulate the living body.

In all embodiments of the vein dissecting device and method disclosed here, the dissecting device and method are specifically implemented to dissect the layer (saphenous fascia), the vein (saphenous vein) and tissue around the vein from surrounding tissue in the living body.

The detailed description above describes embodiments of a blood vessel dissecting device and blood vessel dissecting method representing examples of the invention disclosed here for harvesting a blood vessel (vein) for use in vascular bypass grafting. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A vein harvesting device for harvesting a vein in a body, the vein harvesting device comprising:

an elongated hollow member possessing a distal end portion and a proximal end portion;

a dissecting member that includes a mount connected to the distal end portion of the elongated hollow member and that is configured to dissect a tissue in the body surrounding the vein during harvesting of the vein, the mount of the dissecting member possessing a proximal end portion communicating with the elongated hollow member;

the dissecting member including two spaced apart side portions connected to and projecting away from the mount so that the mount spans between the two side portions and the side portions project downwardly as viewed from a distal end of the dissecting member, each side portion possessing a first end at an end of the side portion farther from the mount and a second end at an end of the side portion closer to the mount;

the dissecting member including two spaced apart holding portions each connected to the first end of a respective one of the side portions and projecting away from the respective side portion, the two holding portions projecting towards one another as viewed from the distal end of the dissecting member, the mount, the two side portions and the two holding portions together surrounding a space that receives a vein being harvested during use of the vein harvesting device, the mount bounding a top of the space as viewed from the distal end of the dissecting member, the side portions bounding sides of the space as viewed from the distal end of the dissecting member, and the holding portions bounding a bottom of the space as viewed from the distal end of the dissecting member; and a pair of spherically-shaped or cone-shaped projections that contact the tissue in the body surrounding the vein during the harvesting of the vein, each spherically-shaped or cone-shaped projecting in a distal direction either from a distal surface of one of the holding portions or from an intersection of one of the holding portions and the respective side portion.

2. The vein harvesting device according to claim 1, wherein each of the projections possesses a center positioned at a location at which the holding portion intersects the respective side portion.

3. The vein harvesting device according to claim 1, wherein each side portion includes a bottom surface, the projection projecting higher than the bottom surface of the respective side portion.

4. The vein harvesting device according to claim 1, wherein each side portion possesses a distal-most end surface, each projection projecting distally beyond the distal-most end surface of the respective side portion.

5. A vein harvesting device for harvesting a vein in a body, the vein harvesting device comprising:

an elongated hollow member possessing a distal end portion and a proximal end portion;

a dissecting member that includes a mount connected to the distal end portion of the elongated hollow member, the dissecting member including a pair of spaced apart side portions connected to and projecting away from the mount so that the mount spans between the two side portions and the side portions project downwardly as viewed from a distal end of the dissecting member, each side portion possessing a first end at an end of the side portion farther from the mount and a second end at an end of the side portion closer to the mount;

the dissecting member including two spaced apart holding portions each connected to the first end of a respective one of the side portions and projecting away form the respective side portion, the two holding portions projecting towards one another as viewed from the distal end of the dissecting member;

the mount, the two side portions and the two holding portions together surrounding a space that receives a vein being harvested during use of the vein harvesting device, the mount bounding a top of the space as viewed from the distal end of the dissecting member, the side portions bounding sides of the space as viewed from the distal end of the dissecting member, and the holding portions bounding a bottom of the space as viewed from the distal end of the dissecting member;

a distal end portion of each side portion possessing a groove that is open at its distal end, extends toward the proximal end portion of the side member, and terminates at a cutting member configured to cut a side branch of the vein during harvesting of the vein; and a projection projecting from each of the side portions of the dissecting member to contact a tissue in the body surrounding the vein during the harvesting of the vein.

6. The vein harvesting device according to claim 5, wherein each of the projections possesses a center positioned at a location at which the holding portion intersects the side portion.

7. The vein harvesting device according to claim 5, wherein each side portion includes a bottom surface, the projection projecting higher than the bottom surface of the respective side portion.

8. The vein harvesting device according to claim 5, wherein each side portion possesses a distal-most end surface, each projection projecting distally beyond the distal-most end surface of the respective side portion.

9. The vein harvesting device according to claim 5, wherein the projections are spherically-shaped projections.

10. The vein harvesting device according to claim 5, wherein the projections are cone-shaped projections.

11. The vein harvesting device according to claim 5, wherein each projection projects in a distal direction from a distal surface of one of the holding portions.

12. The vein harvesting device according to claim 5, wherein each projection projects from an intersection of one of the holding portions and the respective side portion.

13. The vein harvesting device according to claim 5, wherein the projections are spherically-shaped or cone-shaped projections, and each spherically-shaped or cone-shaped projection projecting in a distal direction either from a distal surface of one of the holding portions or from an intersection of one of the holding portions and the respective side portion.

* * * * *